US012181463B2

(12) United States Patent
Zait et al.

(10) Patent No.: US 12,181,463 B2
(45) Date of Patent: Dec. 31, 2024

(54) PERFORMING OPTICAL MEASUREMENTS ON A SAMPLE

(71) Applicant: S.D. Sight Diagnostics Ltd., Tel Aviv (IL)

(72) Inventors: Amir Zait, Rehovot (IL); Arnon Houri Yafin, Jerusalem (IL); Dan Gluck, Kadima (IL); Sharon Pecker, Rehovot (IL); Yochay Shlomo Eshel, Sde Warburg (IL); Sarah Levy Schreier, Tel Aviv (IL); Joseph Joel Pollak, Neve Daniel (IL)

(73) Assignee: S.D. Sight Diagnostics Ltd., Tel Aviv (IL)

( * ) Notice: Subject to any disclaimer, the term of this patent is extended or adjusted under 35 U.S.C. 154(b) by 758 days.

(21) Appl. No.: 17/360,503

(22) Filed: Jun. 28, 2021

(65) Prior Publication Data

US 2021/0325373 A1 Oct. 21, 2021

Related U.S. Application Data

(63) Continuation of application No. 16/099,270, filed as application No. PCT/IL2017/050526 on May 11, 2017, now Pat. No. 11,099,175.

(60) Provisional application No. 62/334,517, filed on May 11, 2016.

(51) Int. Cl.
| | | |
|---|---|---|
| *G01N 33/50* | (2006.01) | |
| *G01N 15/06* | (2024.01) | |
| *G01N 33/49* | (2006.01) | |
| *G01N 33/569* | (2006.01) | |
| *G01N 33/72* | (2006.01) | |
| *G01N 15/01* | (2024.01) | |

(52) U.S. Cl.
CPC ......... *G01N 33/5094* (2013.01); *G01N 15/06* (2013.01); *G01N 33/49* (2013.01); *G01N 33/56972* (2013.01); *G01N 33/721* (2013.01); *G01N 2015/012* (2024.01); *G01N 2015/016* (2024.01)

(58) Field of Classification Search
CPC .............. G01N 15/05; G01N 15/06; G01N 2015/0073; G01N 2015/008; G01N 2015/055; G01N 33/49; G01N 33/491; G01N 33/5094; G01N 33/56972; G01N 33/72; G01N 33/721; Y10T 436/25625
USPC ........... 436/63, 66, 70, 164, 179; 422/82.05, 422/82.09
See application file for complete search history.

(56) References Cited

U.S. PATENT DOCUMENTS

| | | |
|---|---|---|
| 3,203,768 A | 8/1965 | Tiller et al. |
| 3,603,156 A | 9/1971 | Konkol |
| 3,676,076 A | 7/1972 | Grady |
| 3,786,184 A | 1/1974 | Pieters |
| 3,916,205 A | 10/1975 | Kleinerman |
| 3,967,056 A | 6/1976 | Yata et al. |
| 4,030,888 A | 6/1977 | Yamamoto |
| 4,076,419 A | 2/1978 | Kleker |
| 4,097,845 A | 6/1978 | Bacus |
| 4,199,748 A | 4/1980 | Bacus |
| 4,209,548 A | 6/1980 | Bacus |
| 4,350,884 A | 9/1982 | Dieter |
| 4,453,266 A | 6/1984 | Bacus |
| 4,454,235 A | 6/1984 | Johnson |
| 4,494,479 A | 1/1985 | Drury et al. |
| 4,580,895 A | 4/1986 | Patel |
| 4,700,298 A | 10/1987 | Palcic et al. |
| 4,761,381 A | 8/1988 | Blatt et al. |
| 4,774,192 A | 9/1988 | Terminiello et al. |
| 4,803,352 A | 2/1989 | Bierleutgeb |
| 4,849,430 A | 7/1989 | Fleet |
| 4,851,330 A | 7/1989 | Kohne |
| 4,902,101 A | 2/1990 | Fujihara et al. |
| 5,001,067 A | 3/1991 | Coleman et al. |
| 5,064,282 A | 11/1991 | Curtis |
| 5,229,265 A | 7/1993 | Tometsko |
| 5,300,779 A | 4/1994 | Hillman et al. |
| 5,331,958 A | 7/1994 | Oppenheimer |
| 5,430,542 A | 7/1995 | Shepherd et al. |
| 5,470,751 A | 11/1995 | Sakata et al. |
| 5,499,097 A | 3/1996 | Ortyn et al. |
| 5,566,249 A | 10/1996 | Rosenlof et al. |

(Continued)

FOREIGN PATENT DOCUMENTS

| | | |
|---|---|---|
| CA | 2655024 C | 11/2014 |
| CN | 1918501 A | 2/2007 |

(Continued)

OTHER PUBLICATIONS

Communication dated Feb. 22, 2023 issued by the Canadian Patent Office in application No. 3,081,669.
Communication dated Jul. 12, 2023 issued by the Canadian Patent Office in application No. 3,155,820.
Communication dated Jul. 17, 2023 issued by the Canadian Patent Office in application No. 3,155,821.
Communication dated Jul. 3, 2023 issued by the United States Patent and Trademark Office in U.S. Appl. No. 17/568,858.
Communication dated Jun. 22, 2023 issued by the Canadian Office Action in application No. 3, 160,697.
Communication dated Jun. 8, 2023, issued by the Canadian Patent Office in application No. 3, 160,692.

(Continued)

*Primary Examiner* — Maureen Wallenhorst
(74) *Attorney, Agent, or Firm* — Sughrue Mion, PLLC

(57) ABSTRACT

Apparatus and methods are described including measuring hematocrit within a blood sample, by performing a first measurement on a first portion of the blood sample. Mean corpuscular volume in the blood sample is measured, by performing a second measurement on a second portion of the blood sample, the second portion being diluted with respect to the first portion. A red blood cell count per unit volume within the blood sample is determined by dividing the hematocrit measured within the first portion by the mean corpuscular volume measured within the second portion. Other applications are also described.

13 Claims, 7 Drawing Sheets

(56) References Cited

U.S. PATENT DOCUMENTS

| | | | |
|---|---|---|---|
| 5,625,706 A | 4/1997 | Lee et al. |
| 5,663,057 A | 9/1997 | Drocourt et al. |
| 5,671,288 A | 9/1997 | Wilhelm et al. |
| 5,672,861 A | 9/1997 | Fairley et al. |
| 5,674,457 A | 10/1997 | Williamsson et al. |
| 5,745,804 A | 4/1998 | Iwane |
| 5,782,770 A | 7/1998 | Mooradian et al. |
| 5,827,190 A | 10/1998 | Palcic et al. |
| 5,834,217 A | 11/1998 | Levine et al. |
| 5,932,872 A | 8/1999 | Price |
| 5,948,686 A | 9/1999 | Wardlaw et al. |
| 5,978,497 A | 11/1999 | Lee et al. |
| 5,983,120 A * | 11/1999 | Groner ............... G01N 15/06 600/476 |
| 5,985,595 A | 11/1999 | Krider et al. |
| 5,993,702 A | 11/1999 | Davis |
| 6,005,964 A | 12/1999 | Reid et al. |
| 6,027,695 A | 2/2000 | Oldenburg et al. |
| 6,064,474 A | 5/2000 | Lee |
| 6,074,879 A | 6/2000 | Zelmanovic et al. |
| 6,101,404 A | 8/2000 | Yoon et al. |
| 6,235,536 B1 | 5/2001 | Wardlaw |
| 6,262,798 B1 | 7/2001 | Shepherd et al. |
| 6,320,979 B1 | 11/2001 | Melen |
| 6,330,348 B1 | 12/2001 | Kerschmann et al. |
| 6,339,472 B1 | 1/2002 | Hafeman |
| 6,350,613 B1 | 2/2002 | Wardlaw et al. |
| 6,448,024 B1 | 9/2002 | Bruegger |
| 6,519,355 B2 | 2/2003 | Nelson |
| 6,554,788 B1 | 4/2003 | Hunley et al. |
| 6,582,964 B1 | 6/2003 | Samsoondar et al. |
| 6,611,777 B2 | 8/2003 | Samsoondar |
| 6,632,681 B1 | 10/2003 | Chu |
| 6,658,143 B2 | 12/2003 | Hansen |
| 6,664,528 B1 | 12/2003 | Cartlidge et al. |
| 6,711,516 B2 | 3/2004 | Samsoondar |
| 6,799,119 B1 | 9/2004 | Voorhees et al. |
| 6,819,408 B1 | 11/2004 | Scrivens et al. |
| 6,831,733 B2 | 12/2004 | Pettersson |
| 6,834,237 B2 | 12/2004 | Noergaard et al. |
| 6,836,559 B2 | 12/2004 | Abdel-fattah |
| 6,842,233 B2 | 1/2005 | Narisada |
| 6,866,823 B2 | 3/2005 | Wardlaw |
| 6,872,930 B2 | 3/2005 | Cartlidge et al. |
| 6,898,451 B2 | 5/2005 | Wuori |
| 6,903,323 B2 | 6/2005 | Cartlidge et al. |
| 6,929,953 B1 | 8/2005 | Wardlaw et al. |
| 6,949,384 B2 | 9/2005 | Samsoondar |
| 6,955,872 B2 | 10/2005 | Maples et al. |
| 6,956,650 B2 | 10/2005 | Boas |
| 6,989,891 B2 | 1/2006 | Braig et al. |
| 7,027,628 B1 | 4/2006 | Gagnon |
| 7,030,351 B2 | 4/2006 | Wasserman |
| 7,034,883 B1 | 4/2006 | Rosenqvist |
| 7,105,795 B2 | 9/2006 | Cartlidge et al. |
| 7,132,636 B1 | 11/2006 | Cartlidge |
| 7,133,547 B2 | 11/2006 | Marcelpoil |
| 7,151,246 B2 | 12/2006 | Fein et al. |
| 7,155,049 B2 | 12/2006 | Wetzel |
| 7,248,716 B2 | 7/2007 | Fein et al. |
| 7,274,810 B2 | 9/2007 | Reeves et al. |
| 7,283,217 B2 | 10/2007 | Ikeuchi |
| 7,288,751 B2 | 10/2007 | Cartlidge et al. |
| 7,305,109 B1 | 12/2007 | Gagnon |
| 7,324,694 B2 | 1/2008 | Chapoulaud |
| 7,329,537 B2 | 2/2008 | Qiu |
| 7,338,168 B2 | 3/2008 | Cartlidge et al. |
| 7,344,890 B2 | 3/2008 | Perez et al. |
| 7,346,205 B2 | 3/2008 | Walker, Jr. |
| 7,369,696 B2 | 5/2008 | Arini et al. |
| 7,387,898 B1 | 6/2008 | Gordon |
| 7,411,680 B2 | 8/2008 | Chang |
| 7,417,213 B2 | 8/2008 | Krief et al. |
| 7,385,168 B2 | 9/2008 | Cartlidge et al. |
| 7,425,421 B2 | 9/2008 | Dertinger |
| 7,439,478 B2 | 10/2008 | Cartlidge et al. |
| 7,450,223 B2 | 11/2008 | Ikeuchi |
| 7,450,762 B2 | 11/2008 | Morell |
| 7,460,222 B2 | 12/2008 | Kalveram |
| 7,490,085 B2 | 2/2009 | Walker et al. |
| 7,493,219 B1 | 2/2009 | Qi |
| 7,580,120 B2 | 8/2009 | Hamada |
| 7,599,893 B2 | 10/2009 | Sapir |
| 7,601,938 B2 | 10/2009 | Cartlidge et al. |
| 7,602,954 B2 | 10/2009 | Marcelpoil |
| 7,605,356 B2 | 10/2009 | Krief |
| 7,609,369 B2 | 10/2009 | Simon-Lopez |
| 7,630,063 B2 | 12/2009 | Padmanabhan |
| 7,633,604 B2 | 12/2009 | Ikeuchi |
| 7,638,748 B2 | 12/2009 | Krief et al. |
| 7,663,738 B2 | 2/2010 | Johansson |
| 7,668,362 B2 | 2/2010 | Olson |
| 7,692,131 B2 | 4/2010 | Fein et al. |
| 7,697,764 B2 | 4/2010 | Kataoka |
| 7,702,181 B2 | 4/2010 | Gouch |
| 7,706,862 B2 | 4/2010 | Alfano et al. |
| 7,713,474 B2 | 5/2010 | Schulman et al. |
| 7,747,153 B2 | 6/2010 | Ibaraki |
| 7,765,069 B2 | 7/2010 | Ostoich |
| 7,777,869 B2 | 8/2010 | Nerin |
| 7,787,109 B2 | 8/2010 | Dosmann et al. |
| 7,796,797 B2 | 9/2010 | Nakaya et al. |
| 7,863,552 B2 | 1/2011 | Cartlidge et al. |
| 7,869,009 B2 | 1/2011 | Dosmann et al. |
| 7,894,047 B2 | 2/2011 | Hamada |
| 7,911,617 B2 | 3/2011 | Padmanabhan |
| 7,925,070 B2 | 4/2011 | Sumida |
| 7,929,121 B2 | 4/2011 | Wardlaw |
| 7,933,435 B2 | 4/2011 | Hunter |
| 7,936,913 B2 | 5/2011 | Nordell |
| 7,951,599 B2 | 5/2011 | Levine |
| 7,995,200 B2 | 8/2011 | Matsumoto |
| 7,998,435 B2 | 8/2011 | Reed et al. |
| 8,000,511 B2 | 8/2011 | Perz |
| 8,044,974 B2 | 10/2011 | Sumida |
| 8,045,782 B2 | 10/2011 | Li |
| 8,055,471 B2 | 11/2011 | Qi |
| 8,064,680 B2 | 11/2011 | Ramoser |
| 8,077,296 B2 | 12/2011 | Wardlaw |
| 8,081,303 B2 | 12/2011 | Levine |
| 8,105,554 B2 | 1/2012 | Kanigan et al. |
| 8,125,643 B2 | 2/2012 | Hansen |
| D655,421 S | 3/2012 | Lee et al. |
| 8,131,035 B2 | 3/2012 | Grady |
| 8,131,052 B2 | 3/2012 | Alexandrov |
| 8,150,114 B2 | 4/2012 | Svanberg |
| 8,154,713 B2 | 4/2012 | Simon-Lopez |
| 8,165,385 B2 | 4/2012 | Reeves |
| 8,175,353 B2 | 5/2012 | Westphal |
| 8,179,597 B2 | 5/2012 | Namba |
| 8,184,273 B2 | 5/2012 | Dosmann |
| 8,192,995 B2 | 6/2012 | Zhang et al. |
| 8,216,832 B2 | 7/2012 | Battrell et al. |
| 8,224,058 B2 | 7/2012 | Lindberg |
| 8,269,954 B2 | 9/2012 | Levine |
| 8,280,134 B2 | 10/2012 | Hoyt |
| 8,310,659 B2 | 11/2012 | Wardlaw |
| 8,320,655 B2 | 11/2012 | Sarachan |
| 8,327,724 B2 | 12/2012 | Fairs |
| 8,331,642 B2 | 12/2012 | Zerfass |
| 8,339,586 B2 | 12/2012 | Zahniser |
| 8,345,227 B2 | 1/2013 | Zahniser |
| 8,351,676 B2 | 1/2013 | Dai |
| 8,363,221 B2 | 1/2013 | Hansen |
| 8,379,944 B2 | 2/2013 | Grady |
| 8,406,498 B2 | 3/2013 | Ortyn |
| 8,428,331 B2 | 4/2013 | Dimarzio |
| 8,432,392 B2 | 4/2013 | Kim |
| 8,477,294 B2 | 7/2013 | Zahniser |
| 8,481,303 B2 | 7/2013 | Faris et al. |
| 8,488,111 B2 | 7/2013 | Zahniser |
| 8,491,499 B2 | 7/2013 | Choi et al. |
| 8,526,704 B2 | 9/2013 | Dobbe |
| 8,570,496 B2 | 10/2013 | Chen |

(56) References Cited

U.S. PATENT DOCUMENTS

| | | |
|---|---|---|
| 8,582,924 B2 | 11/2013 | De La Torre-bueno |
| 8,638,427 B2 | 1/2014 | Wardlaw |
| 8,712,142 B2 | 4/2014 | Rajpoot |
| 8,736,824 B2 | 5/2014 | Matsui |
| 8,744,165 B2 | 6/2014 | Liu |
| 8,778,687 B2 | 7/2014 | Levine |
| 8,787,650 B2 | 7/2014 | Muragame |
| 8,790,929 B2 * | 7/2014 | Mori .................. G01N 15/131 436/63 |
| 8,792,693 B2 | 7/2014 | Satish |
| 8,837,803 B2 | 9/2014 | Wang et al. |
| 8,849,024 B2 | 9/2014 | Shinoda |
| 8,873,827 B2 | 10/2014 | Mcculloch |
| 8,877,458 B2 | 11/2014 | Maurer |
| 8,878,923 B2 | 11/2014 | Henderson |
| 8,885,154 B2 | 11/2014 | Wardlaw |
| 8,885,912 B2 | 11/2014 | Sui |
| 8,891,851 B2 | 11/2014 | Spaulding |
| 8,922,761 B2 | 12/2014 | Zahniser |
| 8,942,458 B2 | 1/2015 | Takahashi |
| 8,964,171 B2 | 2/2015 | Zahniser |
| 8,992,750 B1 | 3/2015 | Beaty |
| 8,994,930 B2 | 3/2015 | Levine |
| 9,012,868 B2 | 4/2015 | Courtney et al. |
| 9,041,792 B2 | 5/2015 | Van Leeuwen |
| 9,050,595 B2 | 6/2015 | Miller et al. |
| 9,064,301 B2 | 6/2015 | Zie et al. |
| 9,046,473 B2 | 9/2015 | Levine |
| 9,176,121 B2 | 11/2015 | Winkelman et al. |
| 9,186,843 B2 | 11/2015 | Chan et al. |
| 9,240,043 B2 | 1/2016 | Christiansen |
| 9,322,767 B2 | 4/2016 | Ehrenkranz |
| 9,329,129 B2 | 5/2016 | Pollak et al. |
| 9,342,734 B2 | 5/2016 | Lin et al. |
| 9,404,852 B2 | 8/2016 | Braig et al. |
| 9,470,609 B2 | 10/2016 | Wimberger-friedl |
| 9,477,875 B2 | 10/2016 | Ohya |
| 9,522,396 B2 | 12/2016 | Bachelet |
| 9,528,978 B2 | 12/2016 | Yamada |
| 9,588,033 B2 | 3/2017 | Zahniser et al. |
| 9,767,343 B1 | 9/2017 | Jones et al. |
| 9,820,990 B2 | 11/2017 | Pak et al. |
| 9,933,363 B2 | 4/2018 | Danuser et al. |
| 9,934,571 B2 | 4/2018 | Ozaki |
| 9,976,945 B2 | 5/2018 | Kendall et al. |
| 10,024,858 B2 | 7/2018 | Smith et al. |
| 10,061,972 B2 | 8/2018 | Champlin |
| 10,093,957 B2 | 10/2018 | Pollak et al. |
| 10,169,861 B2 | 1/2019 | Ozaki et al. |
| 10,176,565 B2 | 1/2019 | Greenfield |
| 10,281,386 B2 | 5/2019 | Hsu et al. |
| 10,482,595 B2 | 11/2019 | Yorav-Rafael |
| 10,488,644 B2 | 11/2019 | Eshel |
| 10,508,983 B2 | 12/2019 | Kendall et al. |
| 10,640,807 B2 | 5/2020 | Pollak |
| 10,663,712 B2 | 5/2020 | Eshe |
| 10,843,190 B2 | 11/2020 | Bachelet |
| 11,099,175 B2 * | 8/2021 | Zait .................. G01N 33/5094 |
| 11,199,690 B2 | 12/2021 | Eshel |
| 11,609,413 B2 | 3/2023 | Yorav-Raphael et al. |
| 2002/0009711 A1 | 1/2002 | Wada et al. |
| 2002/0028158 A1 | 3/2002 | Wardlaw et al. |
| 2002/0028471 A1 | 3/2002 | Oberhardt |
| 2003/0017085 A1 | 3/2003 | Kercso et al. |
| 2003/0161514 A1 | 8/2003 | Curry |
| 2003/0170613 A1 | 9/2003 | Straus |
| 2003/0197925 A1 | 10/2003 | Hamborg |
| 2003/0224522 A1 | 12/2003 | de Jong |
| 2003/0227612 A1 | 12/2003 | Fein et al. |
| 2003/0227673 A1 | 12/2003 | Nakagawa |
| 2003/0231791 A1 | 12/2003 | Torre-Bueno et al. |
| 2004/0240050 A1 | 2/2004 | Ogihara |
| 2004/0241677 A1 | 2/2004 | Lin et al. |
| 2004/0054283 A1 * | 3/2004 | Corey .................. G01H 5/00 600/438 |
| 2004/0122216 A1 | 6/2004 | Nielsen |
| 2004/0132171 A1 | 7/2004 | Rule et al. |
| 2004/0170312 A1 | 9/2004 | Soenksen |
| 2004/0185447 A1 | 9/2004 | Maples et al. |
| 2004/0218804 A1 | 11/2004 | Affleck et al. |
| 2005/0089208 A1 | 4/2005 | Dong et al. |
| 2005/0109959 A1 | 5/2005 | Wasserman et al. |
| 2005/0175992 A1 | 8/2005 | Aberl et al. |
| 2005/0286800 A1 | 12/2005 | Gouch |
| 2006/0002817 A1 | 1/2006 | Bohm |
| 2006/0003458 A1 | 1/2006 | Golovchenko et al. |
| 2006/0045505 A1 | 3/2006 | Zeineh |
| 2006/0051778 A1 | 3/2006 | Kallick |
| 2006/0063185 A1 | 3/2006 | Vannier |
| 2006/0079144 A1 | 4/2006 | Klisch et al. |
| 2006/0187442 A1 | 8/2006 | Chang et al. |
| 2006/0190226 A1 | 8/2006 | Jojic et al. |
| 2006/0222567 A1 | 10/2006 | Kloepfer et al. |
| 2006/0223052 A1 | 10/2006 | MacDonald et al. |
| 2006/0223165 A1 | 10/2006 | Chang et al. |
| 2007/0252984 A1 | 1/2007 | Van Beek et al. |
| 2007/0054350 A1 | 3/2007 | Walker |
| 2007/0076190 A1 | 4/2007 | Nakaya et al. |
| 2007/0161075 A1 | 7/2007 | Gleich |
| 2007/0172956 A1 | 7/2007 | Magari et al. |
| 2007/0231914 A1 * | 10/2007 | Deng .................. G01N 27/3274 435/287.1 |
| 2007/0243117 A1 | 10/2007 | Wardlaw et al. |
| 2007/0250301 A1 | 10/2007 | Vaisberg et al. |
| 2008/0019584 A1 | 1/2008 | Lindberg et al. |
| 2008/0020128 A1 | 1/2008 | van Ryper |
| 2008/0059135 A1 | 3/2008 | Murugkar et al. |
| 2008/0118399 A1 | 5/2008 | Fleming |
| 2008/0187466 A1 | 8/2008 | Wardlaw et al. |
| 2008/0212069 A1 | 9/2008 | Goldberg et al. |
| 2008/0260369 A1 | 10/2008 | Ibaraki |
| 2008/0273776 A1 | 11/2008 | Krief et al. |
| 2008/0305514 A1 | 12/2008 | Alford et al. |
| 2009/0066934 A1 | 3/2009 | Gao et al. |
| 2009/0074282 A1 | 3/2009 | Pinard et al. |
| 2009/0075324 A1 | 3/2009 | Pettersson |
| 2009/0086314 A1 | 4/2009 | Namba |
| 2009/0088336 A1 | 4/2009 | Burd et al. |
| 2009/0128618 A1 | 5/2009 | Fahn et al. |
| 2009/0185734 A1 | 7/2009 | Lindberg et al. |
| 2009/0191098 A1 | 7/2009 | Beard et al. |
| 2009/0195688 A1 | 8/2009 | Henderson et al. |
| 2009/0213214 A1 | 8/2009 | Yamada |
| 2009/0258347 A1 | 10/2009 | Scott |
| 2009/0269799 A1 | 10/2009 | Winkelman et al. |
| 2009/0291854 A1 | 11/2009 | Wiesinger-Mayr et al. |
| 2010/0003265 A1 | 1/2010 | Scheffler |
| 2010/0068747 A1 | 3/2010 | Herrenknecht |
| 2010/0104169 A1 | 4/2010 | Yamada |
| 2010/0112631 A1 | 5/2010 | Hur et al. |
| 2010/0120129 A1 | 5/2010 | Amshey et al. |
| 2010/0136556 A1 | 6/2010 | Friedberger et al. |
| 2010/0136570 A1 | 6/2010 | Goldberg et al. |
| 2010/0152054 A1 | 6/2010 | Love |
| 2010/0157086 A1 | 6/2010 | Segale et al. |
| 2010/0172020 A1 | 7/2010 | Price |
| 2010/0192706 A1 | 8/2010 | Fairs |
| 2010/0232675 A1 | 9/2010 | Ortyn et al. |
| 2010/0234703 A1 | 9/2010 | Sterling et al. |
| 2010/0253907 A1 | 10/2010 | Korb |
| 2010/0254596 A1 | 10/2010 | Xiong |
| 2010/0256918 A1 | 10/2010 | Chen et al. |
| 2010/0265323 A1 | 10/2010 | Perz |
| 2010/0272334 A1 | 10/2010 | Yamada et al. |
| 2010/0295998 A1 | 11/2010 | Sakai et al. |
| 2010/0300563 A1 | 12/2010 | Ramunas et al. |
| 2011/0007178 A1 | 1/2011 | Kahlman |
| 2011/0009163 A1 | 1/2011 | Fletcher |
| 2011/0030458 A1 | 2/2011 | Park et al. |
| 2011/0059481 A1 | 3/2011 | Wardlaw et al. |
| 2011/0102571 A1 | 5/2011 | Yoneyama |
| 2011/0123398 A1 | 5/2011 | Carrhilo et al. |
| 2011/0144480 A1 | 6/2011 | Lu et al. |
| 2011/0149097 A1 | 6/2011 | Danuser et al. |

(56) References Cited

U.S. PATENT DOCUMENTS

| | | |
|---|---|---|
| 2011/0151502 A1 | 6/2011 | Kendall et al. |
| 2011/0178716 A1 | 7/2011 | Krockenberger et al. |
| 2011/0212486 A1 | 9/2011 | Yamada |
| 2011/0243794 A1 | 10/2011 | Wardlaw |
| 2011/0249910 A1 | 10/2011 | Henderson |
| 2011/0275111 A1 | 11/2011 | Pettigrew et al. |
| 2011/0301012 A1 | 12/2011 | Dolecek et al. |
| 2012/0002195 A1 | 1/2012 | Wu et al. |
| 2012/0021951 A1 | 1/2012 | Hess et al. |
| 2012/0030618 A1 | 2/2012 | Leong et al. |
| 2012/0044342 A1 | 2/2012 | Hing et al. |
| 2012/0058504 A1 | 3/2012 | Li et al. |
| 2012/0092477 A1 | 4/2012 | Kawano et al. |
| 2012/0120221 A1 | 5/2012 | Dong et al. |
| 2012/0169863 A1 | 7/2012 | Bachelet et al. |
| 2012/0225446 A1 | 9/2012 | Wimberger-friedl et al. |
| 2012/0237107 A1 | 9/2012 | Tawfik et al. |
| 2012/0275671 A1 | 11/2012 | Eichhorn et al. |
| 2012/0312957 A1 | 12/2012 | Loney et al. |
| 2012/0320045 A1 | 12/2012 | Yao |
| 2013/0023007 A1 | 1/2013 | Zahniser et al. |
| 2013/0078668 A1 | 3/2013 | Levine et al. |
| 2013/0130262 A1 | 5/2013 | Battrell et al. |
| 2013/0169948 A1 | 7/2013 | Xie |
| 2013/0170730 A1 | 7/2013 | Yu et al. |
| 2013/0176551 A1 | 7/2013 | Wardlaw et al. |
| 2013/0177974 A1 | 7/2013 | Mamaghani et al. |
| 2013/0203082 A1 | 8/2013 | Gonda et al. |
| 2013/0273968 A1 | 10/2013 | Rhoads et al. |
| 2013/0284924 A1 | 10/2013 | Mizuochi et al. |
| 2013/0290225 A1 | 10/2013 | Kamath et al. |
| 2013/0323757 A1 | 12/2013 | Poher |
| 2014/0139625 A1 | 5/2014 | Mathuis et al. |
| 2014/0139630 A1 | 5/2014 | Kowalevicz |
| 2014/0185906 A1 | 7/2014 | Ding et al. |
| 2014/0186859 A1 | 7/2014 | Calderwood et al. |
| 2014/0205176 A1 | 7/2014 | Obrien et al. |
| 2014/0270425 A1 | 9/2014 | Kenny et al. |
| 2014/0273064 A1 | 9/2014 | Smith et al. |
| 2014/0347459 A1 | 11/2014 | Greenfield et al. |
| 2014/0347463 A1 | 11/2014 | Lin et al. |
| 2014/0353524 A1 | 12/2014 | Danuser et al. |
| 2015/0037806 A1 | 2/2015 | Pollak et al. |
| 2015/0124082 A1 | 5/2015 | Kato et al. |
| 2015/0183153 A1 | 7/2015 | Chan et al. |
| 2015/0190063 A1 | 7/2015 | Zakharov et al. |
| 2015/0246170 A1 | 9/2015 | Miao et al. |
| 2015/0278575 A1 | 10/2015 | Allano et al. |
| 2015/0302237 A1 | 10/2015 | Ohya et al. |
| 2015/0316477 A1 | 11/2015 | Pollak et al. |
| 2016/0042507 A1 | 2/2016 | Turner |
| 2016/0146750 A1* | 5/2016 | Hughes .............. G01N 27/3274 204/406 |
| 2016/0187235 A1 | 6/2016 | Fine |
| 2016/0208306 A1 | 7/2016 | Pollak et al. |
| 2016/0246046 A1 | 8/2016 | Yorav-Raphael et al. |
| 2016/0250312 A1 | 9/2016 | Longley et al. |
| 2016/0279633 A1 | 9/2016 | Bachelet et al. |
| 2017/0052110 A1 | 2/2017 | Malissek et al. |
| 2017/0115271 A1 | 4/2017 | Xie et al. |
| 2017/0160185 A1 | 6/2017 | Minemura et al. |
| 2017/0191945 A1 | 7/2017 | Zhang et al. |
| 2017/0218425 A1 | 8/2017 | Chen et al. |
| 2017/0292905 A1 | 10/2017 | Obrien et al. |
| 2017/0307496 A1 | 10/2017 | Zahniser et al. |
| 2017/0326549 A1 | 11/2017 | Jones et al. |
| 2017/0328924 A1 | 11/2017 | Jones et al. |
| 2018/0246313 A1 | 8/2018 | Eshel et al. |
| 2018/0259318 A1* | 9/2018 | Yelin ..................... G01B 9/04 |
| 2018/0296102 A1 | 10/2018 | Satish et al. |
| 2018/0297024 A1 | 10/2018 | Tran |
| 2019/0002950 A1 | 1/2019 | Pollak et al. |
| 2019/0087953 A1 | 3/2019 | Yorav-Rafael |
| 2019/0130567 A1 | 5/2019 | Greenfield |
| 2019/0145963 A1 | 5/2019 | Zait |
| 2019/0266723 A1 | 8/2019 | Blanchard et al. |
| 2019/0302099 A1 | 10/2019 | Pollak |
| 2019/0347467 A1 | 11/2019 | Ohsaka et al. |
| 2020/0034967 A1 | 1/2020 | Yorav-Rafael |
| 2020/0049970 A1 | 2/2020 | Eshel |
| 2020/0111209 A1 | 4/2020 | Greenfield |
| 2020/0249458 A1 | 8/2020 | Eshel et al. |
| 2020/0300750 A1 | 9/2020 | Eshel et al. |
| 2022/0189016 A1 | 6/2022 | Barnes et al. |

FOREIGN PATENT DOCUMENTS

| | | |
|---|---|---|
| CN | 101403650 A | 4/2009 |
| CN | 101501785 A | 8/2009 |
| CN | 102282467 A | 12/2011 |
| EP | 0073551 A2 | 3/1983 |
| EP | 0479231 A1 | 4/1992 |
| EP | 1 381 229 A1 | 1/2004 |
| EP | 1698883 A1 | 9/2006 |
| EP | 2145684 A2 | 1/2010 |
| EP | 2 211 165 A2 | 7/2010 |
| EP | 3001174 A1 | 3/2016 |
| EP | 3123927 | 2/2017 |
| EP | 3482189 A1 | 5/2019 |
| EP | 1 873 232 B1 | 2/2020 |
| GB | 2329014 A | 3/1999 |
| JP | 60-162955 A | 8/1985 |
| JP | 61-198204 A | 9/1986 |
| JP | 7-504038 A | 4/1995 |
| JP | H08-313340 A | 11/1996 |
| JP | 9-54083 A | 2/1997 |
| JP | H11-73903 A | 3/1999 |
| JP | 2000-199845 A | 7/2000 |
| JP | 2002-516982 A | 6/2002 |
| JP | 2004-144526 A | 5/2004 |
| JP | 2004-257768 A | 9/2004 |
| JP | 2006-506607 A | 2/2006 |
| JP | 2006-301270 A | 11/2006 |
| JP | 2007-40814 A | 2/2007 |
| JP | 2009-180539 A | 8/2009 |
| JP | 2009-233927 A | 10/2009 |
| JP | 2009-268432 A | 11/2009 |
| JP | 2011-95225 A | 5/2011 |
| JP | 2013-515264 A | 5/2013 |
| JP | 2013-541767 A | 11/2013 |
| JP | 2014-41139 A | 3/2014 |
| JP | 2015-57600 A | 3/2015 |
| JP | 2016-70658 A | 5/2016 |
| JP | 2016-528506 A | 9/2016 |
| JP | 2017-209530 A | 11/2017 |
| JP | 2018-525611 A | 9/2018 |
| RU | 2402006 C1 | 10/2010 |
| WO | 1985/005446 | 12/1985 |
| WO | 1996/001438 | 1/1996 |
| WO | 1996/012981 | 5/1996 |
| WO | 1996/013615 | 5/1996 |
| WO | 2000/006765 | 2/2000 |
| WO | 2000/052195 | 8/2000 |
| WO | 2000/055572 | 9/2000 |
| WO | 2003/081525 | 2/2003 |
| WO | 2003/056327 | 7/2003 |
| WO | 2003/065358 A2 | 8/2003 |
| WO | 2003/073365 | 9/2003 |
| WO | 2004/020112 A1 | 3/2004 |
| WO | 2004/111610 | 12/2004 |
| WO | 2005/121863 | 12/2005 |
| WO | 2006/121266 | 11/2006 |
| WO | 2008/063135 | 5/2008 |
| WO | 2010/036827 A1 | 4/2010 |
| WO | 2010/056740 | 5/2010 |
| WO | 2010/116341 | 10/2010 |
| WO | 2010/126903 | 11/2010 |
| WO | 2010/137543 A1 | 12/2010 |
| WO | 2011/056658 A1 | 5/2011 |
| WO | 2011/076413 | 6/2011 |
| WO | 2011/123070 | 10/2011 |
| WO | 2011/143075 | 11/2011 |
| WO | 2012/000102 | 1/2012 |
| WO | 2012/029269 | 3/2012 |

(56) References Cited

FOREIGN PATENT DOCUMENTS

| | | |
|---|---|---|
| WO | 2012/030313 | 3/2012 |
| WO | 2012/090198 | 5/2012 |
| WO | 2012/154333 | 11/2012 |
| WO | 2013/041951 | 3/2013 |
| WO | 2013/098821 | 7/2013 |
| WO | 2014/146063 A2 | 9/2014 |
| WO | 2014/159620 | 10/2014 |
| WO | 2014/188405 | 11/2014 |
| WO | 2015/001553 | 1/2015 |
| WO | 2015/029032 | 3/2015 |
| WO | 2015/089632 | 6/2015 |
| WO | 2016/030897 | 3/2016 |
| WO | 2017/195208 | 11/2016 |
| WO | 2016/203320 A2 | 12/2016 |
| WO | 2017/046799 | 3/2017 |
| WO | 2017/168411 | 10/2017 |
| WO | 2017/195205 | 11/2017 |
| WO | 2018/009920 | 1/2018 |
| WO | 2018/102748 A1 | 6/2018 |
| WO | 2019/035084 | 2/2019 |
| WO | 2019/097387 | 5/2019 |
| WO | 2019/102277 | 5/2019 |
| WO | 2019/198094 | 10/2019 |
| WO | 2021/079305 | 4/2021 |
| WO | 2021/079306 | 4/2021 |
| WO | 2021/116962 A1 | 6/2021 |

OTHER PUBLICATIONS

Communication dated Jun. 9, 2023 issued by the Canadian Patent Office in application No. 3,160,688.
Communication dated Mar. 17, 2023 issued by the United States Patent and Trademark Office in U.S. Appl. No. 17/083,647.
Communication dated Mar. 2, 2023 issued in the Canadian Patent Office in application No. 3,018,536.
Communication dated Mar. 20, 2023 issued by the European Patent Office in application No. 22209948.3.
Communication dated Mar. 27, 2023 issued by the Brazilian Patent Office in application No. BR122020017765-9.
Communication dated Mar. 27, 2023 issued by the United States Patent and Trademark Office in U.S. Appl. No. 16/763,810.
Communication dated Mar. 3, 2022 issued by the United States Patent and Trademark Office in U.S. Appl. No. 17/063,320.
Communication dated Mar. 3, 2023 issued by the United States Patent and Trademark Office in U.S. Appl. No. 17/082,483.
Communication dated Mar. 7, 2023 issued by the Japanese Patent Office in application No. 2021-157849.
Communication dated Nov. 25, 2022 issued by the United States Patent and Trademark Office in U.S. Appl. No. 17/082,483.
Hirota, T., et al., "Kusanon AR Poisoning Complicated by Heinz Body Hemolytic Anemia", Japanese Association for Acute Medicine Magazine, vol. 12, No. 12, Dec. 15, 2001, (1 page total).
Notice of Allowance dated Apr. 12, 2023 issued by the United States Patent and Trademark Office in U.S. Appl. No. 16/088,321.
Onodera, M., "Organ Derangement", Medicina, Sep. 9, 2005, vol. 42, No. 9, pp. 1582-1584 (5 pages total).
Sawhney, A. K., et al., "Erythrocyte Alterations Induced by Malathion in Channa punctatus (Bloch)", Bull. Environ. Contam. Toxicol., 2000, vol. 64, pp. 395-405.
Takakusaki, T., "Shape Change of Red Cell Ghost and ATP", The KITAKANTO Medical Journal, 1960, vol. 10, Issue 4, pp. 522-531 (11 pages total).
Tyulina, O., et al., "Erythrocyte and plasma protein modification in alcoholism: A possible role of acctaldehyde", Biochimica et Biophysica Acta, vol. 1762, 2006, pp. 558-563 (6 pages total).
Non-Final Office Action dated Oct. 6, 2021, which issued during the prosecution of U.S. Appl. No. 17/063,320.
An Extended European Search Report issued for European Patent Application No. 21164814.2 on Jun. 9, 2021.
Third Office Action dated Jul. 12, 2021 which issued during the prosecution of Chinese Patent Application No. 201680053431.1.
Non-Final Office Action dated Jul. 27, 2021, which issued during the prosecution of U.S. Appl. No. 16/851,686.
Non-Final Office Action dated Aug. 19, 2021, which issued during the prosecution of U.S. Appl. No. 16/098,893.
Non-Final Office Action dated Sep. 1, 2021 which issued during the prosecution of U.S. Appl. No. 16/088,321.
First Office Action dated Aug. 4, 2021 which issued during the prosecution of Chinese Patent Application No. 201780027908.3.
An Examination Report dated Mar. 4, 2021 which issued during the prosecution of Indian Patent Application No. 201817036130.
An Examination Report dated May 5, 2021 which issued during the prosecution of Indian Patent Application No. 201817012117.
Notice of Allowance dated Aug. 3, 2021, which issued during the prosecution of U.S. Appl. No. 16/851,410.
An International Search Report and Written Opinion for Application No. PCT/IB2020/061731 issued on Feb. 10, 2021.
Invitation to pay fees and Partial Search Report issued for PCT Application No. PCT/IB2020/061732 on Mar. 10, 2021.
Invitation to pay fees and Partial Search Report issued for PCT Application No. PCT/IB2020/061736 on Mar. 12, 2021.
Invitation to pay fees and Partial Search Report issued for PCT Application No. PCT/IB2020/061728 on Mar. 15, 2021.
International Search Report issued for PCT Application No. PCT/IB2020/061724 on Mar. 10, 2021.
An International Search Report and Written Opinion for PCT Application No. PCT/IB2020/061732 mailed on May 7, 2021.
International Search Report and Written Opinion for PCT Application No. PCT/IB2020/061728 mailed on May 7, 2021.
International Search Report and Written Opinion for PCT Application No. PCT/IB2020/061736 mailed on May 3, 2021.
Non-Final Office Action dated Jun. 17, 2021 which issued during the prosecution of U.S. Appl. No. 16/851,410.
A Final Office Action dated Jun. 17, 2021 which issued during the prosecution of U.S. Appl. No. 16/088,321.
Notice of Allowance dated May 19, 2021 which issued during the prosecution of U.S. Appl. No. 16/099,270.
A Restriction Requirement issued by the USPTO on Oct. 19, 2020 for U.S. Appl. No. 16/099,270.
An Office Action dated Jul. 12, 2022, which issued during the prosecution of U.S. Appl. No. 16/088,321.
An Office Action dated Aug. 2, 2022, which issued during the prosecution of Japanese Patent Application No. 2021-145455.
An Examination Report dated Aug. 25, 2022, which issued during the prosecution of Australian Patent Application No. 2017263807.
An Office Action dated Aug. 30, 2022 which issued during the prosecution of Japanese Patent Application No. 2020-526176.
An Office Action dated Sep. 13, 2022 which issued during the prosecution of Japanese Patent Application No. 2021-157849.
Hideto Miura, "How to regard as how to consider the poikilocyte in urine an erroneous decision factor", Modern Medical Laboratory, Sep. 1, 2002, vol. 30, No. 9, pp. 862-864 (6 pages total).
Jun Hashimoto, "Morphological Studies of Urinary Red Blood Cells in Renal and Urinary Tract Disorders (II) Use of Wright's Stain in Differential Diagnosis between Renal and Urinary Tract Disorders" Kawasaki Medical Congress Magazine, Mar. 1989, vol. 15, No. 1, pp. 94-101 (9 pages total).
D F Birch et al., "The research on the differential diagnosis of the kidney urinary tract obstacle by glomerular or non-glomerular", Lancet, Oct. 20, 1979, vol. 2, No. 8147, pp. 845-846 (3 pages total).
A First Examination Report dated Sep. 19, 2022, which issued during the prosecution of Indian Patent Application No. 201817040226.
An Office Action dated Oct. 3, 2022 which issued during the prosecution of U.S. Appl. No. 16/763,810.
An Office Action dated Oct. 25, 2022 which issued during the prosecution of Canadian Application No. 2,998,829 (SDX044).
An Office Action dated Oct. 5, 2022 which issued during the prosecution of Brazilian Application No. 112018005099-7.
An Office Action dated Nov. 25, 2022 which issued during the prosecution of Brazilian Application No. 122020017765-9.
An Office Action dated Dec. 9, 2022 which issued during the prosecution of U.S. Appl. No. 17/083,647.

(56) References Cited

OTHER PUBLICATIONS

An Office Action dated Dec. 28, 2022 which issued during the prosecution of Russian Patent Application No. 2022112399.
An Office Action dated Dec. 28, 2022 which issued during the prosecution of Russian Patent Application No. 2022112393.
An Office Action dated Jan. 6, 2023 which issued during the prosecution of U.S. Appl. No. 17/063,320.
An Office Action dated Sep. 2, 2022 which issued during the prosecution of U.S. Appl. No. 17/063,320.
An Office Action dated Jan. 5, 2023 which issued during the prosecution of Chinese Patent Application No. 201880079888.9.
An Examination Report dated Jan. 23, 2023, which issued during the prosecution of Australian Patent Application No. 2022200112.
An Office Action dated Jan. 19, 2023 which issued during the prosecution of U.S. Appl. No. 17/490,767.
Notice of Allowance dated Nov. 5, 2021, which issued during the prosecution of U.S. Appl. No. 16/851,410.
Notice of Allowance dated Nov. 10, 2021, which issued during the prosecution of U.S. Appl. No. 16/851,686.
Supplemental Notice of Allowance dated Nov. 12, 2021, which issued during the prosecution of U.S. Appl. No. 16/851,686.
A European Examination Report issued for European Patent Application No. 17728277.9 on Dec. 23, 2021.
Notice of Allowance dated Jan. 21, 2022, which issued during the prosecution of U.S. Appl. No. 16/098,893.
An Office Action dated Feb. 16, 2022 which issued during the prosecution of U.S. Appl. No. 16/088,321.
An Office Action dated May 6, 2022 which issued during the prosecution of U.S. Appl. No. 16/763,810.
A Non-Final Office Action dated May 26, 2022 which issued during the prosecution of U.S. Appl. No. 17/083,775.
An Office Action dated May 31, 2022 which issued during the prosecution of U.S. Appl. No. 17/083,659.
Examination Report issued by the Indian Patent Office on Jun. 28, 2022 in Indian Patent Application No. 202047019700.
United States Second Notice of Allowance issued Aug. 23, 2023 in U.S. Appl. No. 17/490,767.
United States Notice of Allowance issued May 15, 2023 in U.S. Appl. No. 17/490,767.
An Examination Report issued Aug. 16, 2023, in Australian Patent Application No. 2018369859.
Canadian Office Action issued Aug. 25, 2023 in Application No. 3,160,702.
United States Office Action issued May 30, 2023 in U.S. Appl. No. 17/082,615.
A Hearing Notice issued by the Indian Patent Office on Aug. 29, 2023 for IN 201817012117.
A Hearing Notice issued by the Indian Patent Office on Sep. 1, 2023 for IN 201817036130.
United States Office Action issued Sep. 14, 2023 in U.S. Appl. No. 17/083,647.
United States Office Action issued Sep. 14, 2023 in U.S. Appl. No. 17/063,320.
Office Action dated Dec. 7, 2023 which issued during the prosecution of Canadian Application No. 3,081,669.
A Summons to an Oral Hearing issued by the European Patent Office on Oct. 5, 2023 for Application No. 17728277.9.
A Decision to Refuse issued on Oct. 3, 2023 for Japanese Patent Application No. 2021-157849.
Canadian Office Action issued Oct. 13, 2023 in Application No. 2,998,829.
United States Notice of Allowance issued Oct. 12, 2023 in U.S. Appl. No. 17/568,858.
United States Office Action issued Oct. 17, 2023 in U.S. Appl. No. 17/082,615.
A Hearing Notice issued by the Indian Patent Office on Nov. 9, 2023 for IN 201817040226.
Canadian Office Action issued Dec. 19, 2023 in Application No. 3,018,536.
An Office Action dated Dec. 21, 2023 which issued during the prosecution of Brazilian Application No. 112018 072627 3.
United States Office Action issued Jan. 9, 2024 in U.S. Appl. No. 18/203,109.
"Blood specimens:Microscopic Examination", Centers for Disease Control and Prevention CDC, Diagnostic Procedures, 2009, <http://www.dpd.cdc.gov/dpdx/HTML/Frames/DiagnosticProcedures/body_dp_bloodexamin.htm>.
Agero, U., Mesquita, L.G., Neves, B.R.A., Gazzinelli, R.T. and Mesquita, O.N., 2004. Defocusing microscopy. Microscopy research and technique, 65(3), pp. 159-165.
Ahirwar, Neetu et al., "Advanced Image Analysis Based System for Automatic Detection and Classification of Malarial Parasite in Blood Images," International Journal of Information Technology and Knowledge Management Jan.-Jun. 2012, vol. 5, No. 1, pp. 59-64, Serial Publications Pvt. Ltd, India.
An International Preliminary Report on Patentability dated Feb. 28, 2017, which issued during the prosecution of Applicant's PCT/IL2015/050864.
An International Search Report and a Written Opinion dated Jul. 27, 2012 for International Application No. PCT/IL2011/000973.
An International Search Report and a Written Opinion both dated Apr. 18, 2013, for International Application No. PCT/IL2012/050556.
An International Search Report and a Written Opinion both dated Feb. 12, 2015, for International Application No. PCT/IL2014/050770.
An International Search Report and a Written Opinion both dated Jan. 15, 2016, for International Application No. PCT/IL2015/050864.
An International Search Report and a Written Opinion both dated Jan. 23, 2017. which issued during the prosecution of Applicant's PCT/IL2016/051025.
An International Search Report and a Written Opinion both dated Oct. 30, 2014, for International Application No. PCT/IL2014/050585.
An International Search Report and a Written Opinion both dated Sep. 24, 2014 for International Application No. PCT/IL2012/050423.
An International Search Report and Written Opinion in International Application No. PCT/IB2018/058861, issued on Apr. 8, 2019.
An International Search Report and Written Opinion, dated Aug. 30, 2017 from the International Bureau in counterpart International application No. PCT/IL2017/050526.
An International Search Report and Written Opinion, dated Aug. 8, 2017 from the International Bureau in counterpart International application No. PCT/IL2017/050523.
An International Search Report and Written Opinion, dated May 18, 2017 from the International Bureau in counterpart International application No. PCT/IL2017/050363.
An Office Action dated Apr. 2, 2015, which issued during the prosecution of U.S. Appl. No. 13/338,291.
An Office Action dated Apr. 4, 2019 which issued during the prosecution of U.S. Appl. No. 14/914,329.
An Office Action dated Aug. 4, 2017. which issued during the prosecution of U.S. Appl. No. 14/369,251.
An Office Action dated Feb. 22, 2018 which issued during the prosecution of U.S. Appl. No. 14/369,251.
An Office Action dated Jan. 10, 2018. which issued during the prosecution of U.S. Appl. No. 15/083,610.
An Office Action dated Jan. 28, 2019 which issued during the prosecution of U.S. Appl. No. 15/174,490.
An Office Action dated Jul. 11, 2017. which issued during the prosecution of U.S. Appl. No. 15/174,490.
An Office Action dated Jun. 13, 2017. which issued during the prosecution of U.S. Appl. No. 14/285,672.
An Office Action dated Jun. 15, 2018 from the United States Patent and Trademark Office in copending U.S. Appl. No. 14/369,251.
An Office Action dated Jun. 29, 2018 from the United States Patent and Trademark Office in copending U.S. Appl. No. 15/174,490.
An Office Action dated Jun. 4, 2019, which issued during the prosecution of U.S. Appl. No. 14/369,251.

(56) References Cited

OTHER PUBLICATIONS

An Office Action dated Jun. 5, 2019, which issued during the prosecution of U.S. Appl. No. 15/174,490.
An Office Action dated Mar. 2, 2017. which issued during the prosecution of U.S. Appl. No. 14/369,251.
An Office Action dated Nov. 16, 2018 which issued during the prosecution of U.S. Appl. No. 14/914,329.
An Office Action dated Oct. 29, 2014, which issued during the prosecution of U.S. Appl. No. 13/338,291.
An Office Action dated Oct. 5, 2016, which issued during the prosecution of U.S. Appl. No. 14/285,672.
An Office Action dated Sep. 25, 2015, which issued during the prosecution of U.S. Appl. No. 13/338,291.
Anand, A., et al. "Automatic Identification of Malaria-Infected RBC with Digital Holographic Microscopy Using Correlation Algorithms." Photonics Journal, IEEE 4.5 (2012): 1456-1464.
Bacus, J.W., 1985. Cytometric approaches to red blood cells. Pure and Applied AL Chemistry, 57(4), pp. 593-598.
Biéler, Sylvain et al. "Improved detection of Trypanosoma brucei by lysis of red blood cells, concentration and LED fluorescence microscopy"; Acta Tropica; vol. 121, Issue 2, Feb. 2012, pp. 135-140.
Bravo-Zanoguera, M.E., Laris, C.A., Nguyen, L.K., Oliva, M. and Price, J.H., 2007. Dynamic autofocus for continuous-scanning time-delay-and-integration image acquisition in automated microscopy. Journal of biomedical optics, 12(3), pp. 034011-034011.
Brenner et al., An Automated Microscope for Cytologic Research a Preliminary Evaluation, [The Journal of Histochecmistry and Cytochemistry, vol. 24, No. 1, pp. 100-111, 1976.
Briggs, C., et al., "Continuing developments with the automated platelet count", Blackwell Publishing Ltd, International Journal of Laboratory Hematology, Jan. 18, 2007, pp. 77-91, vol. 29 (15 pages total).
Centers for Disease Control and Prevention. DPDx—Laboratory Identification of Parasitic Diseases of Public Health Concern <http://www.cdc.gov/dpdx/diagnosticProcedures/blood/microexam.html>, Nov. 29, 2013.
Cervantes, Serena, Jacques Prudhomme, David Carter, Krishna G Gopi, Qian Li, Young-Tae Chang, and Karine G Le Roch, High-content live cell imaging with RNA probes: advancements in high-throughput antimalarial drug discovery, BMC Cell Biology 2009, 10:45, https://bmcmolcellbiol.biomedcentral.com/track/pdf/10.1186/1471-2121-10-45 (Jun. 10, 2009).
Chiodini, P. L. et al., "Rapid diagnosis of malaria by fluorescence microscopy"; The Lancet, vol. 337, Issue 8741, p. 624-625, Mar. 9, 1991.
Chong, Shau Poh, Shilpa Pant, and Nanguang Chen. "Line-scan Focal Modulation Microscopy for Rapid Imaging of Thick Biological Specimens." SPIE/OSA/IEEE Asia Communications and Photonics. International Society for Optics and Photonics, 2011.
Emma Eriksson et al: "Automated focusing of nuclei for time lapse experiments on single cells using holographic optical tweezers", Optics Express, vol. 17, No., 7, Mar. 24, 2009, pp. 5585-5594.
F. Boray Tek et al. "Parasite detection and identification for automated thin blood film malaria diagnosis"; Computer Vision and Image Understanding vol. 114, Issue 1, Jan. 2010, pp. 21-32.
Fohlen-Walter, Anne PhD, et al., "Laboratory Identification of Cryoglobulinemia From Automated Blood Cell Counts, Fresh Blood Samples, and Blood Films", American Society for Clinical Pathology, Am J Clin Pathol, 2002, pp. 606-614, vol. 117 (9 pages total).
Frean, John. "Microscopic Determination of Malaria Parasite Load: Role of Image Analysis." Microscopy: Science, technology, Applications, and Education (2010): 862-866.
Gallo, V., Skorokhod, O.A., Schwarzer, e, and Arese, P. "Simultaneous determination of phagocytosis of Plasmodium falciparum-parasitized and non-parasitized red blood cells by flow cytometry"; Malaria Journal 2012 11:428.
Garcia, et al. "Laboratory Diagnosis of Blood-borne Parasitic Diseases; Approved Guideline"; NCCLS Documents M115-a, Jun. 2000.

Gordon, Andrew et al. "Single-cell quantification of molecules" Nature Methods 4, Jan. 21, 2007, pp. 175-181.
Gordon, Andrew et al. Supplementary Note to Gordon et al: "Single-cell quantification of molecules" Nature Methods, Jan. 21, 2007, pp. 1-35.
Groen, F.C.A., et al. "A comparison of different focus functions for use in autofocus algorithms" Cytometry, Alan Liss, New York, US vol. 6, No. 2, Mar. 1, 1985 (Mar. 1, 1985) pp. 81-91.
Guy, Rebecca, Paul Liu, Peter Pennefather and Ian Crandall, "The use of fluorescence enhancement to improve the microscopic diagnosis of falciparum malaria", Malaria Journal 2007 6:89, https://malariajournal.biomedcentral.com/articles/10.1186/1475-2875-6-89, (Jul. 9, 2007).
Houri-Yafin, A., et al. "An enhanced computer vision platform for clinical diagnosis of malaria" Malaria Control and Elimination, 2016, p. 138, vol. 5, Issue 1, omics International, India.
Jager et al. "Five-minute Giemsa stain for rapid detection of malaria parasites in blood smears", Tropical Doctor, vol. 41, pp. 33-35, Jan. 2011.
Jahanmehr,S A H et al., " Simple Technique for Fluorescence Staining of Blood Cells with Acridine Orange", Journal of Clinical Pathology, Feb. 12, 1987, pp. 926-929 (4 pages total).
Joanny, Fanny, Helda Jana, and Benjamin Mordmllera, "In Vitro Activity of Fluorescent Dyes against Asexual Blood Stages of Plasmodium falciparum" DOI: 10.1128/AAC.00709-12, date unknown.
Kawamoto, F. and P.F.Billingsley, "Rapid diagnosis of malaria by fluorescence microscopy", Parasitology Today, 8.2 (1992): 69-71.
Kawamoto,F. "Rapid diagnosis of malaria by fluorescence microscopy with light microscope and interference filter", The Lancet, vol. 337, pp. 200-202, Jan. 26, 1991.
Keiser, J. et al., "Acridine Orange for malaria diagnosis: its diagnostic performance, its promotion and implementation in Tanzania, and the implications for malaria control", Annals of Tropical Medicine and parasitology, 96.7 (2002): 643-654.
Knesel, "Roche Image Analysis Systems, Inc.", Acta Cytologica, vol. 40, pp. 60-66, (1996).
Kumar, Amit et al. "Enhanced Identification of Malarial Infected Objects using Otsu Algorithm from Thin Smear Digital Images." International Journal of Latest Research in Science and Technology vol. 1,Issue 2:pp. 159-163, Jul.-Aug. 2012).
Le, Minh-Tam et al., "A novel semi-automatic image processing approach to determine Plasmodium falciparum parasitemia in Giemsa-stained thin blood smears", BMC Cell Biology, published Mar. 28, 2008.
Leif, "Methods for Preparing Sorted Cells as Monolayer Specimens", Springer Lab Manuals, Section 7—Chapter 5 pp. 592-619, (2000).
Life Technologies Corporation, "Counting blood cells with Countless Automated Cell Counter" found at http://www.lifetechnologies.com/content/dam/LifeTech/migration/files/cell-tissue-analysis/pdfs.par.83996.file.dat/w-082149-countless-application-blood-cells.pdf, four pages, (2009).
Matcher, S.J., et al. "Use of the water absorption spectrum to quantify tissue chromophore concentration changes in near-infrared spectroscopy", Physics in Medicine & Biology, vol. 39, No. 1, 1994 pp. 177-196, IOP Publishing Ltd., UK.
Mendiratta, D.K. et al. Evaluation of different methods for diagnosis of P. falciparum malaria; Indian J Med Microbiol. Jan. 2006;24(1):49-51.
Merchant et al. , "Computer-Assisted Microscopy", The essential guide to image processing, Chapter 27, pp. 777-831, Academic Press, (2009).
Moody , "Rapid Diagnostic Tests for Malaria Parasites", Clinical Microbiology Reviews, vol. 15, No. 1, pp. 66-78, 12 (2002).
Moon S, Lee S, Kim H, Freitas-Junior LH, Kang M, Ayong L, et al. (2013) An Image Analysis Algorithm for Malaria Parasite Stage Classification and Viability Quantification. PLoS One 8(4): e61812. https://doi.org/10.1371/journal.pone.0061812.
Notice of Allowance dated Dec. 30, 2015 U.S. Appl. No. 14/440,864.
Notice of Allowance dated Jan. 11, 2016, which issued during the prosecution of U.S. Appl. No. 14/440,864.
Notice of Allowance dated Jan. 19, 2016, which issued during the prosecution of U.S. Appl. No. 13/338,291.

(56) References Cited

OTHER PUBLICATIONS

Notice of Allowance dated Mar. 10, 2016, which issued during the prosecution of U.S. Appl. No. 13/338,291.
Notice of Allowance dated Mar. 20, 2019, which issued during the prosecution of U.S. Appl. No. 15/506,997.
Ortyn, William E.,et al. "Extended Depth of Field Imaging for High Speed Cell Analysis." Cytometry Part A 71.4, 2007): 215-231.
Osibote, O. A., et al. "Automated focusing in bright-field microscopy for tuberculosis detection", Journal of Microscopy 240.2 (2010)pp. 155-163.
Pasini, Erica M. et al. "A novel live-dead staining methodology to study malaria parasite viability"; Malaria Journal 2013 12:190.
Piruska, Aigars et al., "The autofluorescence of plastic materials and chips measured under laser irradiation" Lab on a Chip, 2005, 5, 1348-1354, published Nov. 1, 2005.
Poon et al., "Automated Image Detection and Segmentation in Blood Smears", [Cytometry 1992 13:766-774].
Purwar, Yashasvi, et al. "Automated and Unsupervised Detection of Malarial Parasites in Microscopic Images." Malaria Journal 10.1 (2011): 364.
Rappaz, Benjamin et al., "Comparative study of human erythrocytes by digital holographic microscopy, confocal microscopy, and impedance volume analyzer" Cytometry Part A, 2008, vol. 73, Issue 10, pp. 895-903, John Wiley & Sons, US.
Roma, P. M. S., et al. "Total three-dimensional imaging of phase objects using defocusing microscopy: Application to red blood cells." Applied Physics Letters 104,25 (2014): 251107.
Ross, Nichoals E., et al., "Automated image processing method for the diagnosis and classification of malaria on thin blood smears", Medical and Biological Engineering and Computing, May 2006, vol. 44, Issue 5, pp. 427-436, Springer Publishing Company, US.
Sheikh , H., Bin Zhu, Micheli-Tzanakou, E. (1996) "Blood cell identification using neural networks." Proceedings of the IEEE 22nd Annual Northeast Bioengineering Conference; pp. 119-120.
Shen, Feimo, Louis Hodgson and Klaus Hahn, "Digital autofocus method for automated microscopy", Methods in Enzymology vol. 414, 2006, pp. 620-632.
Shute G. T. and T. M. Sodeman, "Identification of malaria parasites by fluorescence microscopy and acridine orange staining", Bulletin of the World Health Organ. 1973; 48(5): 591-596.
Sun, Yu, S. Duthaler and B.J. Nelson, "Autofocusing algorithm selection in computer microscopy", 2005 IEEE/RSJ International Conference on Intelligent Robots and Systems.
Tek, F. Boray, Andrew G. Dempster, and Izzet Kale. "Computer Vision for Microscopy Diagnosis of Malaria." Malaria Journal 8.1 (2009): 153.
Thung, Ferdian, and Iping Supriana Suwardi. "Blood Parasite Identification Using Feature Based Recognition." Electrical Engineering and Informatics (ICEEI), 2011 International Conference on. IEEE, 2011.
U.S. Appl. No. 61/870,106 filed Aug. 26, 2013.
U.S. Appl. No. 62/042,388, filed Aug. 27, 2014.
UNITAID Malaria Diagnostic Technology and Market Landscape, 2nd Edition (2014).
Wissing, Frank et al. "Illumination of the Malaria Parasite Plasmodium falciparum Alters Intracellular pH", Implications for Live Cell Imaging; published Jul. 24, 2002, JBS Papers in Press, vol. 277 No. 40, pp. 27747-37755.
Wright, J H. "A Rapid Method for the Differential Staining of Blood Films and Malarial Parasites" Journal of medical research vol. 7,1 (1902): 138-44.
Wu, Caicai et al., "Feasibility study of the spectroscopic measurement of oxyhemoglobin using whole blood without pre-treatment", The Analyst, Mar. 1998, pp. 477-481, vol. 123 (5 pages total).
Wu, Qiang, Fatima Mechant, and Kenneth Castleman. Microscope Image Processing. Chapter 16, Autofocusing, pp. 441-467, Academic Press, 2010.
Xu, Lili, Asok Chaudhuri, "Plasmodium yoelii: A differential fluorescent technique using Acridine Orange to identify infected erythrocytes and reticulocytes in Duffy knockout mouse", Experimental Parasitology, vol. 110, Issue 1, May 2005, pp. 80-87, https://www.sciencedirect.com/science/article/pii/S001448940500038X, (May 31, 2005).
Yang, Ming, and Li Luo. "A Rapid Auto-Focus Method in Automatic Microscope." Signal Processing, 2008. ICSP 2008. 9th International Conference on. IEEE,2008.
Yao, LN et al. "Pathogen identification and clinical diagnosis for one case infected with Babesia". Zhongguo ji sheng chong xue yu ji sheng chong bing za zhi Chinese journal of parasitology parasitic diseases, Aug. 2012.
Yazdanfar, S., Kenny, K.B., Tasimi, K., Corwin, A.D., Dixon, E.L. and Filkins, R.J., 2008. Simple and robust image-based autofocusing for digital microscopy. Optics express, 16(12), pp. 8670-8677.
Zahniser et al., Automated Slide Preparation System for the Clinical Laboratory, Cytometry, vol. 26, No. 10, pp. 60-64, (1996).
A European Examination Report dated Dec. 9, 2019. which issued during the prosecution of Applicant's European App No. 16782094.3.
Notice of Allowance dated Mar. 2, 2020, which issued during the prosecution of U.S. Appl. No. 16/657,473.
A European Examination Report dated Feb. 1, 2019. which issued during the prosecution of Applicant's European App No. 17717000.8.
A European Examination Report dated Sep. 3, 2019. which issued during the prosecution of Applicant's European App No. 17717000.8.
A European Examination Report dated Apr. 8, 2020. which issued during the prosecution of Applicant's European App No. 17717000.8.
A European Examination Report dated Apr. 6, 2020. which issued during the prosecution of Applicant's European App No. 17726036.1.
A European Examination Report dated Feb. 11, 2020. which issued during the prosecution of Applicant's European App No. 17728277.9.
An Office Action dated Aug. 24, 2020 for U.S. Appl. No. 16/098,893.
A Chinese Office Action and dated May 22, 2020. which issued during the prosecution of Chinese Application No. 201680053431.1.
A Restriction Requirement issued by the USPTO on Aug. 24, 2020 for U.S. Appl. No. 16/088,321.
Saraswat, et al. "Automated microscopic image analysis for leukocytes identification: A survey", ABV—Indian Institute of Information Technology and Management, Gwalior, India, date unknown.
Hiremath, P.S,. et al., "Automated Identification and Classification of White Blood Cells (Leukocytes) in Digital Microscopic Images", IJCA Special Issue on "Recent Trends in Image Processing and Pattern Recognition" RTIPPR, 2010.
Witt, et al. "Establishing traceability of photometric absorbance values for accurate measurements of the haemoglobin concentration in blood.", Metrologia 50 (2013) 539-548.
Putzu, et al., "Leucocyte classification for leukaemia detection using image processing techniques.", Artificial Intelligence in Medicine, vol. 63, No. 3, Nov. 1, 2014.
Varga, et al., "An automated scoring procedure for the micronucleus test by image analysis,", Mutagenesis vol. 19 No. 5 pp. 391-397, 2004.
Ran, Qiong et al. "Spatial-spectral blood cell classification with microscopic hyperspectral imagery", Proc. SPIE 10461, AOPC 2017: Optical Spectroscopy and Imaging, 1046102 (Oct. 24, 2017).
Omucheni et al. "Application of principal component analysis to multispectral-multimodal optical image analysis for malaria diagnostics", Malaria Journal 2014, 13:485 http://www.malariajournal.com/content/13/1/485.
Ben-Suliman—2018—Computerized Counting-Based System for Acute Lymphoblastic Leukemia Detection in Microscopic Blood Images: 27th International Conference on Artificial Neural Networks, Rhodes, Greece, Oct. 4-7, 2018, Proceedings, Part II.
An Office Action dated Dec. 8, 2020 for Japanese Patent Application No. 2018/512961.
An Examination Report issued on Dec. 7, 2020 for Australian Patent Application No. 2016322966.
An Office Action dated Jan. 11, 2021 for U.S. Appl. No. 16/098,893.

(56) References Cited

OTHER PUBLICATIONS

An Examination Report issued on Apr. 29, 2021 for Australian Patent Application No. 2016322966.
International Search Report issued for PCT Application No. PCT/IB2020/059924 on Mar. 22, 2021.
International Search Report issued for PCT Application No. PCT/IB2020/059925 on Mar. 26, 2021.
Invitation to pay fees and Partial Search Report issued for PCT Application No. PCT/IB2020/059924 on Jan. 28, 2021.
Invitation to pay fees and Partial Search Report issued for PCT Application No. PCT/IB2020/059925 on Feb. 4, 2021.
A Japanese Office Action dated Mar. 30, 2021. which issued during the prosecution of Application No. 2018/558180.
An Office Action dated Mar. 9, 2021 for U.S. Appl. No. 16/088,321.
An Office Action dated Jan. 29, 2021 for U.S. Appl. No. 16/099,270.
A European Search Report dated Dec. 14, 2016 which issued during the prosecution of Applicant's European App No. 14800352.8.
A European Search Report dated Mar. 23, 2017. which issued during the prosecution of Applicant's European App No. 14839661.7.
An Office Action dated Dec. 24, 2018 which issued during the prosecution of Indian Patent Application No. 3592/2012.
An Office Action dated Jan. 31, 2019 which issued during the prosecution of Indian Patent Application No. 5069/DELNP/2012.
An Office Action dated Mar. 23, 2018 which issued during the prosecution of Indian Patent Application No. 4263/DELNP/2014.
Bovik, Alan C., et. "The Essential Guide to Image Processing", Chapter 27, "Computer Assisted Microscopy", pp. 777-831; Academic Press, 2009.
Price Jeffrey H. and David A. Gough, "Comparison of phase☐contrast and fluorescence digital autofocus for scanning microscopy", Cytometry 16.4 (1994) 283-297.
Vink, J.P. et al., "An automatic vision☐based malaria diagnosis system", Journal of Microscopy 250.3 (2013):166-178.
A Final Office Action dated Jun. 17, 2021 which issued during the prosecutio of U.S. Appl. No. 16/088,321.
Notice of Allowance issued for U.S. Appl. No. 16/763,810 on Feb. 8, 2024.
United States Office Action dated Feb. 29, 2024 in U.S. Appl. No. 17/083,647.
Canadian Office Action dated Mar. 4, 2024 in Application No. 3022770.
Canadian Office Action dated Jan. 12, 2023 in Application No. 3022770.
International Search Report and Written Opinion dated Mar. 11, 2024 in Application No. PCT/IB2023/062469.
Canadian Office Action dated Mar. 6, 2024 in Application No. 3160688.
Canadian Office Action dated Mar. 11, 2024 in Application No. 3160692.
United States Office Action dated Mar. 22, 2024 in U.S. Appl. No. 17/360,503.
Canadian Office Action dated Apr. 3, 2024 in Application No. 3160697.
Canadian Office Action dated Apr. 19, 2024 in Application No. 3155820.
New Zealand Office Action dated Apr. 23, 2024 in Application No. 787743.
New Zealand Office Action dated Apr. 24, 2024 in Application No. 787745.
European Office Action dated Apr. 29, 2024 in Application No. 20800326.9.
European Office Action dated May 6, 2024 in Application No. 20 800 325.1.
United States Office Action dated May 7, 2024 in U.S. Appl. No. 17/770,339.
European Office Action dated May 8, 2024 in Application No. 20828314.3.
Kerem Delikoyun, et al., "2 Deep learning-based cellular image analysis for intelligent medical diagnosis", De Gruyter, 2021, (4 pages) https://www.degruyter.com/document/doi/10.1515/9783110668322-002/html.
C.Briggs, et al., "ICSH Guidelines for the evaluation of blood cell analysers including those used for differential leucocyte and reticulocyte counting", International Journal of Laboratory Hematology, 2014, vol. 36, pp. 613-627 (15 pages).
An Office Action dated May 16, 2024 which issued during the prosecution of U.S. Appl. No. 17/063,320.
An Office Action dated May 29, 2024 which issued during the prosecution of Korean Application No. 10-2022-7017082.
A Chinese Office Action dated May 9, 2024 which issued during the prosecution of Application No. 202080085933.9.
Notice of Allowance issued for Canadian Application No. 3,155,821 on May 21, 2024.
An Office Action dated May 29, 2024 which issued during the prosecution of Korean Application No. 10-2022-7017081.

\* cited by examiner

PERFORMING OPTICAL MEASUREMENTS ON A SAMPLE

CROSS-REFERENCE TO RELATED APPLICATIONS

The present application is a continuation of U.S. Ser. No. 16/099,270 to Zait issued as U.S. Pat. No. 11,099,175), which is a US national phase application of PCT Application No. PCT/IL2017/050526 to Zait (published as WO 17/195208), filed May 11, 2017, which claims priority from U.S. Provisional Patent Application No. 62/334,517 to Zait, filed May 11, 2016, entitled "Method and Apparatus for Estimating Dilution and Concentration."

The present application is related to PCT Application No. PCT/IL2017/050523 to Pollak (published as WO 17/195205), filed May 11, 2017, entitled "Sample carrier for optical measurements," which claims priority from U.S. Provisional Patent Application No. 62/334,521 to Pollak, filed May 11, 2016, entitled "Sample carrier for optical measurements."

The above-referenced applications are incorporated herein by reference.

FIELD OF EMBODIMENTS OF THE INVENTION

Some applications of the presently disclosed subject matter relate generally to analyzing a biological sample, and in particular, to analyzing a blood sample by performing optical measurements.

BACKGROUND

Several methods exist for quantifying parameters in a sample (such as, a blood sample). In some such methods, the sample is diluted before being analyzed. For example, a blood sample may be diluted in order to increase visibility of components of the sample within microscopic images of the sample, and/or staining substances may be added to the blood sample, in order to stain given components within the sample.

In some cases, samples are analyzed using more than one type of measuring device. For example, a microscope is sometimes used in order to analyze individual cells within the sample, whereas imaging devices, such as spectral cameras, are used to analyze the sample on a bulk level (e.g., by performing optical absorption, transmittance, fluorescence, and/or luminescence measurements).

SUMMARY OF EMBODIMENTS

In accordance with some applications of the present invention, a portion of a blood sample is diluted using a dilution technique, such as a technique as described in US 2015/0316477 to Pollak, which is incorporated herein by reference. The blood sample portion is typically imaged using a microscope system (which may be manual or automated). For some applications, the microscope images are analyzed (e.g. manually, or using a computer processor that runs suitable computer software) to identify different blood cells.

For some applications of the present invention, variation and/or errors that occur in a dilution process are accounted for. Typically, an error of 10 percent in the dilution factor may correspond directly to a 10 percent error in the count of, for example, red blood cell per unit volume (e.g., per microliter) of blood. Such errors in dilution can originate from a number of sources. Illustrative examples of sources of such errors (which are not intended to limit the scope of the present invention) include pipetting inaccuracy or error, calibration inaccuracy or error, mixing inaccuracy or error, etc. Therefore, in accordance with some applications of the present invention, a measurement is made on a source sample portion (e.g., an undiluted blood sample portion) from which the diluted sample portion is extracted. This measurement typically corresponds to at least one of the measurements measured on the diluted sample portion. For example, the measurement performed on the source sample portion may include measurement of: hemoglobin content, white blood cell content, red blood cell content, hematocrit, content of a specific white blood cell type, platelet content, and/or any measurand that is measured or that can be inferred for the diluted sample portion. For some applications, a normalization factor is determined, the normalization factor being a property of the source sample portion to which other measurements are correlated (e.g. the number of red blood cells per unit area or per unit volume in the source sample portion). Typically, measurands within the sample (e.g., within the source sample portion) are measured based upon the normalization factor, as described in further detail hereinbelow.

For some applications, hematocrit is measured by performing a first measurement on a blood sample, and mean corpuscular volume within the blood sample is measured, by performing a second measurement on the blood sample. For example, hematocrit may be measured using the microhematocrit method (in which the blood is centrifuged), and or by performing ultrasonic and/or impedance measurements on a first portion of the blood sample, and the mean corpuscular volume may be measured by analyzing microscopic images that are acquired of a second portion of the blood sample. Typically, the second portion of the sample is diluted with respect to the first portion of the blood sample, e.g. in order to improve visibility of the individual cells, for the purpose of staining the second portion of the sample, and/or for a different reason. For some applications, based on the relationship between the hematocrit and the mean corpuscular volume, a relationship between the first portion of the sample and second portion of the sample is determined. For some applications, a parameter of the source sample portion is determined, based on the relationship between the hematocrit and the mean corpuscular volume. Typically, the red blood cell count (e.g., count per unit volume) within the sample is determined by dividing the hematocrit by the mean corpuscular volume. For some applications, counts of one or more additional components within the sample (e.g., red blood cells of a given type, white blood cells, white blood cells of a given type, circulating tumor cells, platelets, platelets of a given type, bacteria, pathogens, pathogens of a given type, reticulocytes, and/or Howell-Jolly bodies) are determined, based on the red blood cell count within the sample. For example, a ratio between the red blood cell count and the counts of the one or more additional components within a portion of the sample may be determined, by analyzing a microscopic image of the portion of the sample. The counts of the one or more additional components may then be determined, based on the red blood cell count within the sample and the ratio between the red blood cell count and the counts of the one or more additional components within the portion of the sample.

For some applications, hemoglobin concentration is measured by performing a first measurement on a blood sample, and mean corpuscular hemoglobin within the blood sample is measured, by performing a second measurement on the blood sample. For example, hemoglobin concentration may be measured by performing optical density measurements on a first portion of the blood sample, and the mean corpuscular hemoglobin may be measured by analyzing microscopic images that are acquired of a second portion of the blood sample. Typically, the second portion of the sample is diluted with respect to the first portion of the blood sample, e.g. in order to improve visibility of the individual cells, and/or for the purpose of staining the second portion of the sample, and/or for a different reason. For some applications, based on the relationship between the hemoglobin concentration and the mean corpuscular hemoglobin, a relationship between the first portion of the sample and second portion of the sample is determined. For some applications, a parameter of the source sample portion is determined, based on the relationship between the hemoglobin concentration and the mean corpuscular hemoglobin. Typically, the red blood cell count (e.g., count per unit volume) within the sample is determined by dividing the hemoglobin concentration by the mean corpuscular hemoglobin. For some applications, counts of one or more additional components within the sample (e.g., red blood cells of a given type, white blood cells, white blood cells of a given type, circulating tumor cells, platelets, platelets of a given type, bacteria, pathogens, pathogens of a given type, reticulocytes, and/or Howell-Jolly bodies) are determined, based on the red blood cell count within the sample. For example, a ratio between the red blood cell count and the counts of the one or more additional components within a portion of the sample may be determined, by analyzing a microscopic image of the portion of the sample. The counts of the one or more additional components may then be determined, based on the red blood cell count within the sample and the ratio between the red blood cell count and the counts of the one or more additional components within the portion of the sample.

For some applications of the present invention, two or more measurements (which are typically optical measurements) are performed upon a biological sample. Typically, the biological sample is a blood sample. For some applications, a bulk-level measurand of the sample is measured, by performing a first measurement on the sample, and a cellular-level measurand of the sample is measured, by performing a second measurement on the sample. For the purpose of the present applications, the term "cellular-level measurand" should be understood to mean a measurand that relates to one or more parameters of individual cells or other non-dissolved components within the sample, such as, mean corpuscular volume, mean corpuscular hemoglobin, mean platelet volume, and/or red blood cell distribution width, etc. Measurement of a cellular-level measurand typically involves a first step of identifying individual cells or other non-dissolved components within the sample (e.g., identifying such components within a microscopic image), and a second step of identifying a parameter of such individual identified components. Typically, a cellular-level measurand is measured by analyzing one or more microscopic images of the sample. For the purpose of the present applications, the term "bulk-level measurand" should be understood to mean a measurand that relates a parameter of the sample as a whole, and that does not require the two steps of identifying individual cells or other non-dissolved components within the sample, and identifying a parameter of such individual identified components. For example, such a measurand may include the optical density of a given component (which is measured by performing a measurement on a bulk volume of the sample, e.g., even after performing lysis of individual components within the bulk volume), a count per unit volume of a given component (which is typically measured by identifying such components, but does not require identifying a parameter of individual identified components), and/or the concentration of a given component (such as, red blood cell concentration, hemoglobin concentration, white blood cell concentration, platelet concentration, and/or hematocrit). Typically, bulk-level measurands are measured by performing a measurement on a bulk volume of the sample. For example, such measurements may include ultrasonic, impedance, optical absorption, transmittance, fluorescence, microscopic and/or luminescence measurements that are performed on a bulk volume of the sample. Typically, a parameter of the sample is determined, based on a relationship between the bulk-level measurand and the cellular-level measurand.

For some applications, first and second optical measurements are performed on a sample, using one or more optical measurement devices under respective sets of measuring conditions that are different from each other. A measurand of the sample is measured based upon the first optical measurement, and a measurand of the sample is measured based upon the second optical measurement. In accordance with respective applications, the measurand that is measured based upon the second optical measurement is the same as the measurand that is measured based upon the first optical measurement, or is different from the measurand that is measured based upon the first optical measurement. In accordance with respective applications, the first and second optical measurements are performed on the same portion of the sample, or on different portions of the sample. For some applications, one of the optical measurements is performed on a portion of the sample that is diluted with respect to a portion of the sample upon which the other optical measurement is performed.

Typically, based on a relationship between the measurand measured based upon the first optical measurement and the measurand measured based upon the second optical measurement, a relationship between the measuring conditions of the one or more optical measurement devices that were used to perform the first and second optical measurements is determined. For example, the first and second optical measurements may be performed on respective portions of the sample that are disposed in respective portions of one or more sample chambers having respective dimensions (e.g., respective heights). For some such applications, a relationship between dimensions of the respective portions of the one or more sample chambers is determined, based on the relationship between the measurand measured based upon the first optical measurement and the measurand measured based upon the second optical measurement. Alternatively or additionally, based on the relationship between the measurand measured based upon the first optical measurement and the measurand measured based upon the second optical measurement, the field of view from which one of the first and second optical measurements (e.g., a microscopic image) was measured is determined, and/or the level of magnification at which one of the first and second optical measurements (e.g., a microscopic image) was measured is determined. For some applications, the first and second measurements are normalized with respect to one another. Subsequently, a parameter of the sample is determined based upon the normalization of the first and second measurements with respect to one another.

There is therefore provided, in accordance with some applications of the present invention, a method for use with a blood sample, the method including:

measuring hemoglobin concentration within at least a portion of the blood sample, by performing a first measurement on the blood sample;

measuring mean corpuscular hemoglobin in the blood sample, by performing a second measurement on the blood sample; and determining a parameter of the blood sample, based on a relationship between the concentration of hemoglobin and the mean corpuscular hemoglobin.

In some applications, determining the parameter of the blood sample includes normalizing the first and second measurements with respect to each other, based on the relationship between the hemoglobin concentration and the mean corpuscular hemoglobin.

In some applications, performing the first measurement on the blood sample includes performing an optical density measurement on the blood sample.

In some applications, measuring hemoglobin concentration within at least the portion of the blood sample includes measuring the hemoglobin concentration within a first portion of the blood sample, measuring mean corpuscular hemoglobin in the blood sample includes measuring mean corpuscular hemoglobin within a second portion of the blood sample, and determining the parameter of the sample includes determining a relationship between the first portion of the sample and second portion of the sample, based on the relationship between the hemoglobin concentration and the mean corpuscular hemoglobin.

In some applications, determining the parameter of the sample includes determining a count of a component of the blood selected from the group consisting of: red blood cells, red blood cells of a given type, white blood cells, white blood cells of a given type, circulating tumor cells, platelets, platelets of a given type, bacteria, pathogens, pathogens of a given type, reticulocytes, and Howell-Jolly bodies.

In some applications, determining the parameter of the sample includes determining a concentration of a component of the blood selected from the group consisting of: hemoglobin, red blood cells, red blood cells of a given type, white blood cells, white blood cells of a given type, circulating tumor cells, platelets, platelets of a given type, bacteria, pathogens, pathogens of a given type, reticulocytes, and Howell-Jolly bodies.

In some applications, determining the parameter of the sample includes determining a hematocrit of the sample.

In some applications, measuring the hemoglobin concentration includes measuring the hemoglobin concentration within a first portion of the blood sample, and measuring mean corpuscular hemoglobin in the blood sample includes measuring mean corpuscular hemoglobin within a second portion of the blood sample that is diluted with respect to the first portion of the blood sample.

In some applications, determining the parameter of the blood sample includes determining a normalization factor by determining a property of the first portion of the sample portion for using as a reference to which measurements within the second portion can be correlated.

In some applications, determining the parameter of the blood sample, includes determining a red blood cell count within the sample, by dividing the hemoglobin concentration by the mean corpuscular hemoglobin.

In some applications, determining the parameter of the blood sample, further includes determining counts of one or more components within the sample, based on the red blood cell count within the sample.

In some applications, determining the counts of one or more components within the sample, includes:

determining a ratio between the red blood cell count and the counts of the one or more components within a portion of the sample, by analyzing a microscopic image of the portion of the sample, and determining the count of the one or more components based on the red blood cell count within the sample and the ratio between the red blood cell count and the counts of the one or more components within the portion of the sample.

There is further provided, in accordance with some applications of the present invention, apparatus for use with a blood sample, the apparatus including:

at least one computer processor configured to:

measure hemoglobin concentration within at least a portion of the blood sample, by performing a first measurement on the blood sample, measure mean corpuscular hemoglobin in the blood sample, by performing a second measurement on the blood sample, and determine a parameter of the blood sample, based on a relationship between the concentration of hemoglobin and the mean corpuscular hemoglobin.

There is further provided, in accordance with some applications of the present invention, a computer software product, for use with a blood sample, the computer software product including a non-transitory computer-readable medium in which program instructions are stored, which instructions, when read by a computer cause the computer to perform the steps of:

measuring hemoglobin concentration within at least a portion of the blood sample, by performing a first measurement on the blood sample;

measuring mean corpuscular hemoglobin in the blood sample, by performing a second measurement on the blood sample; and determining a parameter of the blood sample, based on a relationship between the concentration of hemoglobin and the mean corpuscular hemoglobin.

There is further provided, in accordance with some applications of the present invention, a method for use with a blood sample, the method including:

measuring hematocrit in the blood sample, by performing a first measurement on the blood sample;

measuring mean corpuscular volume in the blood sample, by performing a second measurement on the blood sample; and determining a parameter of the blood sample, based on a relationship between the hematocrit and the mean corpuscular volume.

In some applications, determining the parameter of the blood sample includes normalizing the first and second measurements with respect to each other, based on the relationship between the hematocrit and the mean corpuscular volume.

In some applications, performing the first measurement on the blood sample includes performing a measurement on the blood sample selected from the group consisting of: an ultrasonic measurement, and an impedance measurement.

In some applications, performing the first measurement on the blood sample includes centrifuging the blood sample.

In some applications, performing the second measurement includes performing the second measurement by analyzing a microscopic image of a portion of the blood sample.

In some applications, measuring the hematocrit includes measuring the hematocrit on a first portion of the blood sample, measuring mean corpuscular volume in the blood sample includes measuring mean corpuscular volume upon a second portion of the blood sample, and determining the parameter of the sample includes determining a relationship between the first portion of the sample and second portion of the sample, based on the relationship between the hematocrit and the mean corpuscular volume.

In some applications, determining the parameter of the sample includes determining a count of a component of the blood selected from the group consisting of: red blood cells, red blood cells of a given type, white blood cells, white blood cells of a given type, circulating tumor cells, platelets, platelets of a given type, bacteria, pathogens, pathogens of a given type, reticulocytes, and Howell-Jolly bodies.

In some applications, determining the parameter of the sample includes determining a concentration of a component of the blood selected from the group consisting of: hemoglobin, red blood cells, red blood cells of a given type, white blood cells, white blood cells of a given type, circulating tumor cells, platelets, platelets of a given type, bacteria, pathogens, pathogens of a given type, reticulocytes, and Howell-Jolly bodies.

In some applications, measuring the hematocrit includes measuring the hematocrit on a first portion of the blood sample, and measuring mean corpuscular volume in the blood sample includes measuring mean corpuscular volume upon a second portion of the blood sample that is diluted with respect to the first portion of the blood sample.

In some applications, determining the parameter of the blood sample includes determining a normalization factor by determining a property of the first portion of the sample portion for using as a reference to which measurements within the second portion can be correlated.

In some applications, determining the parameter of the blood sample includes determining a red blood cell count within the sample by dividing the hematocrit by the mean corpuscular volume.

In some applications, determining the parameter of the blood sample further includes determining counts of one or more components within the sample, based on the red blood cell count within the sample.

In some applications, determining the counts of one or more components within the sample, includes:
  determining a ratio between the red blood cell count and the counts of the one or more components within a portion of the sample, by analyzing a microscopic image of the portion of the sample, and
  determining the count of the one or more components based on the red blood cell count within the sample and the ratio between the red blood cell count and the counts of the one or more components within the portion of the sample.

There is further provided, in accordance with some applications of the present invention, apparatus for use with a blood sample, the apparatus including:
  at least one computer processor configured to:
    measure hematocrit in the blood sample, by performing a first measurement on the blood sample;
    measure mean corpuscular volume in the blood sample, by performing a second measurement on the blood sample, and
    determine a parameter of the blood sample, based on a relationship between the hematocrit and the mean corpuscular volume.

There is further provided, in accordance with some applications of the present invention, a computer software product, for use with a blood sample, the computer software product including a non-transitory computer-readable medium in which program instructions are stored, which instructions, when read by a computer cause the computer to perform the steps of:
  measuring hematocrit in the blood sample, by performing a first measurement on the blood sample;
  measuring mean corpuscular volume in the blood sample, by performing a second measurement on the blood sample; and
  determining a parameter of the blood sample, based on a relationship between the hematocrit and the mean corpuscular volume.

There is further provided, in accordance with some applications of the present invention, a method for use with a first portion of a blood sample and a second portion of the blood sample that is diluted with respect to the first portion of the blood sample, the method including:
  measuring relative amounts of first and second components within the first portion of the blood sample;
  measuring a measurand within the second portion of the blood sample; and
  determining a parameter of the blood sample based upon a relationship between the relative amounts of first and second components within the first portion of the blood sample, and the measurand within the second portion of the blood sample.

In some applications, measuring relative amounts of first and second components within the first portion of the blood sample includes analyzing a microscopic image of the first portion of the blood sample.

In some applications, measuring relative amounts of first and second components within the first portion of the blood sample includes measuring relative amounts of at least two components within the first portion of the blood sample, the two components being selected from the group consisting of: all white blood cell types, neutrophils, eosinophils, basophils, lymphocytes, monocytes, and white blood cell precursors.

In some applications, measuring relative amounts of first and second components within the first portion of the blood sample includes measuring relative amounts of at least two components within the first portion of the blood sample, the two components being selected from the group consisting of: red blood cells, reticulocytes, intracellular bodies, red blood cells having a given morphology, and Howell-Jolly bodies.

In some applications, measuring relative amounts of first and second components within the first portion of the blood sample includes measuring relative amounts of given types of platelets within the first portion of the blood sample.

In some applications, measuring the measurand within the second portion of the sample includes measuring an absolute count of cells of a given type within the second portion of the blood sample.

In some applications, measuring the measurand within the second portion of the sample includes measuring a concentration of a given component within the second portion of the blood sample.

In some applications, measuring the measurand within the second portion of the sample includes performing a bulk-level measurement upon the second portion of the blood sample.

There is further provided, in accordance with some applications of the present invention, apparatus for use with a blood sample, the apparatus including:
at least one computer processor configured to:
measure relative amounts of first and second components within the first portion of the blood sample,
measure a measurand within the second portion of the blood sample, and
determine a parameter of the blood sample based upon a relationship between the relative amounts of first and second components within the first portion of the blood sample, and the measurand within the second portion of the blood sample.

There is further provided, in accordance with some applications of the present invention, a computer software product, for use with a blood sample, the computer software product including a non-transitory computer-readable medium in which program instructions are stored, which instructions, when read by a computer cause the computer to perform the steps of:
measuring relative amounts of first and second components within the first portion of the blood sample;
measuring a measurand within the second portion of the blood sample; and
determining a parameter of the blood sample based upon a relationship between the relative amounts of first and second components within the first portion of the blood sample, and the measurand within the second portion of the blood sample.

There is further provided, in accordance with some applications of the present invention, a method for use with a biological sample, the method including:
measuring a bulk-level measurand of the sample, by performing a first measurement on the sample;
measuring a cellular-level measurand of the sample, by performing a second measurement on the sample; and
determining a parameter of the sample, based on a relationship between the bulk-level measurand and the cellular-level measurand.

In some applications, determining the parameter of the blood sample includes normalizing the first and second measurements with respect to each other, based on the relationship between the bulk-level measurand and the cellular-level measurand.

In some applications, measuring the bulk-level measurand includes determining an optical density of a given component within the sample.

In some applications, measuring the cellular-level measurand includes analyzing a microscopic image of the sample.

In some applications, performing the first measurement on the sample includes performing the first measurement on the sample using a first set of measuring conditions, performing the second measurement on the sample includes performing the second measurement on the sample using a second set of measuring conditions, and determining the parameter of the sample includes determining a relationship between the measuring conditions that were used to perform the first and second measurements, based on the relationship between the bulk-level measurand and the cellular-level measurand.

In some applications, performing the first measurement includes performing the first measurement on a first portion of the sample, and performing the second measurement includes performing the second measurement upon the first portion of the sample.

In some applications, performing the first measurement includes performing the first measurement on a first portion of the sample, and performing the second measurement includes performing the second measurement upon a second portion of the sample that is different from the first portion of the sample. In some applications, determining the parameter of the sample includes determining a relationship between the first portion of the sample and second portion of the sample, based on the relationship between the bulk-level measurand and the cellular-level measurand. In some applications, performing the second measurement upon the second portion of the sample includes performing the second measurement upon a second portion of the sample that is diluted with respect to the first portion of the sample. In some applications, determining the parameter of the sample includes determining a normalization factor by determining a property of the first portion of the sample portion for using as a reference to which measurements within the second portion can be correlated. In some applications, determining the parameter of the sample includes determining a dilution ratio by which the second portion of the sample is diluted with respect to the first portion of the sample.

In some applications, the biological sample includes a blood sample, and determining the parameter of the sample includes determining a parameter of the blood sample.

In some applications:
measuring the bulk-level measurand of the sample includes measuring hematocrit of the blood sample;
measuring the cellular-level measurand of the sample includes measuring mean corpuscular volume of the blood sample; and
determining the parameter of the sample includes determining the parameter of the sample, based on a relationship between the hematocrit and the mean corpuscular volume.

In some applications:
measuring the bulk-level measurand of the sample includes measuring hemoglobin concentration within at least a portion of the blood sample;
measuring the cellular-level measurand of the sample includes measuring mean corpuscular hemoglobin of the blood sample; and
determining the parameter of the sample includes determining the parameter of the sample, based on a relationship between the hemoglobin concentration and the mean corpuscular hemoglobin.

There is further provided, in accordance with some applications of the present invention, apparatus for use with a biological sample, the apparatus including:
at least one computer processor configured to:
measure a bulk-level measurand of the sample, by performing a first measurement on the sample,
measure a cellular-level measurand of the sample, by performing a second measurement on the sample, and
determine a parameter of the sample, based on a relationship between the bulk-level measurand and the cellular-level measurand.

There is further provided, in accordance with some applications of the present invention, a computer software product, for use with a biological sample, the computer software product including a non-transitory computer-readable medium in which program instructions are stored, which instructions, when read by a computer cause the computer to perform the steps of:
    measuring a bulk-level measurand of the sample, by performing a first measurement on the sample;
    measuring a cellular-level measurand of the sample, by performing a second measurement on the sample; and
    determining a parameter of the sample, based on a relationship between the bulk-level measurand and the cellular-level measurand.

There is further provided, in accordance with some applications of the present invention, a method for use with a biological sample, the method including:
    performing first and second optical measurements on the sample, using one or more optical measurement devices under respective sets of measuring conditions that are different from each other;
    measuring a measurand of the sample, based upon the first optical measurement;
    measuring a measurand of the sample, based upon the second optical measurement; and
    based on a relationship between the measurand measured based upon the first optical measurement and the measurand measured based upon the second optical measurement, determining a relationship between the measuring conditions of the one or more optical measurement devices that were used to perform the first and second optical measurements.

In some applications, the biological sample includes a blood sample, and performing first and second optical measurements on the sample includes performing first and second optical measurements on the blood sample.

In some applications:
    performing first and second optical measurements on a sample includes performing first and second optical measurements on respective portions of the sample that are disposed in respective portions of one or more sample chambers having respective dimensions; and
    determining the relationship between the measuring conditions of the one or more optical measurement devices that were used to perform the first and second optical measurements includes determining a relationship between dimensions of the respective portions of the one or more sample chambers.

In some applications, performing the first and second optical measurements on the sample includes performing at least one of the first and second optical measurements by acquiring an image of at least a portion of the sample, and determining the relationship between the measuring conditions of the one or more optical measurement devices that were used to perform the first and second optical measurements includes determining a field of view of the image.

In some applications, performing the first and second optical measurements on the sample includes performing at least one of the first and second optical measurements by acquiring an image of at least a portion of the sample, and determining the relationship between the measuring conditions of the one or more optical measurement devices that were used to perform the first and second optical measurements includes determining a level of magnification of the image.

In some applications:
    measuring the measurand of the sample, based upon the first optical measurement includes measuring a given measurand of the sample, based upon the first optical measurement;
    measuring the measurand of the sample, based upon the second optical measurement includes measuring the same given measurand of the sample, based upon the second optical measurement; and
    determining the relationship between the measuring conditions of the one or more optical measurement devices that were used to perform the first and second optical measurements includes determining the relationship between the measuring conditions of the one or more optical measurement devices that were used to perform the first and second optical measurements, based upon a relationship the given measurand as measured based upon the first optical measurement, and the given measurand as measured based upon the second optical measurement.

In some applications, performing the first optical measurement includes performing the first optical measurement using a given optical measurement device, and performing the second optical measurement includes performing the second optical measurement using the same given optical measurement device.

In some applications, performing the first optical measurement includes performing the first optical measurement using a first optical measurement device, and performing the second optical measurement includes performing the second optical measurement using a second optical measurement device that is different from the first optical measurement device.

In some applications:
    performing the first optical measurement includes performing the first optical measurement using a first optical measurement device that is configured to measure a parameter of one or more components within the sample, the parameter being selected from the group consisting of: optical absorption, transmittance, fluorescence, and luminescence; and
    performing the second optical measurement includes performing the second optical measurement using a microscope configured to acquire a microscopic image of the sample.

In some applications:
    measuring the measurand of the sample, based upon the first optical measurement includes measuring a first measurand of the sample, based upon the first optical measurement; and
    measuring the measurand of the sample, based upon the second optical measurement includes measuring a second measurand of the sample that is different from the first measurand, based upon the second optical measurement; and
    determining the relationship between the measuring conditions of the one or more optical measurement devices that were used to perform the first and second optical measurements includes determining the relationship between the measuring conditions of the one or more optical measurement devices that were used to perform the first and second optical measurements, based upon a relationship between the first and second measurands.

In some applications, measuring the first measurand includes measuring a bulk-level measurand of the sample, and measuring the second measurand includes measuring a cellular-level measurand of the sample.

There is further provided, in accordance with some applications of the present invention, apparatus for use with a biological sample, the apparatus including:

at least one computer processor configured to:
  perform first and second optical measurements on the sample, using one or more optical measurement devices under respective sets of measuring conditions that are different from each other,
  measure a measurand of the sample, based upon the first optical measurement,
  measure a measurand of the sample, based upon the second optical measurement, and
  based on a relationship between the measurand measured based upon the first optical measurement and the measurand measured based upon the second optical measurement, determine a relationship between the measuring conditions of the one or more optical measurement devices that were used to perform the first and second optical measurements.

There is further provided, in accordance with some applications of the present invention, a computer software product, for use with a biological sample, the computer software product including a non-transitory computer-readable medium in which program instructions are stored, which instructions, when read by a computer cause the computer to perform the steps of:
  performing first and second optical measurements on a sample, using one or more optical measurement devices under respective sets of measuring conditions that are different from each other;
  measuring a measurand of the sample, based upon the first optical measurement;
  measuring a measurand of the sample, based upon the second optical measurement; and
  based on a relationship between the measurand measured based upon the first optical measurement and the measurand measured based upon the second optical measurement, determining a relationship between the measuring conditions of the one or more optical measurement devices that were used to perform the first and second optical measurements.

There is further provided, in accordance with some applications of the present invention, a method for use with a biological sample, the method including:
  performing first and second optical measurements on the sample, using one or more optical measurement devices under respective sets of measuring conditions that are different from each other;
  measuring a measurand of the sample, based upon the first optical measurement;
  measuring a measurand of the sample, based upon the second optical measurement;
  normalizing the measurand measured based upon the first optical measurement and the measurand measured based upon the second optical measurement, with respect to each other; and
  determining a parameter of the sample based upon at least one of the normalized measurand measured based upon the first optical measurement and the normalized measurand measured based upon the second optical measurement.

There is further provided, in accordance with some applications of the present invention, apparatus for use with a biological sample, the apparatus including:
  at least one computer processor configured to:
    perform first and second optical measurements on the sample, using one or more optical measurement devices under respective sets of measuring conditions that are different from each other,
    measure a measurand of the sample, based upon the first optical measurement,
    measure a measurand of the sample, based upon the second optical measurement,
    normalize the measurand measured based upon the first optical measurement and the measurand measured based upon the second optical measurement, with respect to each other, and
    determine a parameter of the sample based upon at least one of the normalized measurand measured based upon the first optical measurement and the normalized measurand measured based upon the second optical measurement.

There is further provided, in accordance with some applications of the present invention, a computer software product, for use with a biological sample, the computer software product including a non-transitory computer-readable medium in which program instructions are stored, which instructions, when read by a computer cause the computer to perform the steps of:
  performing first and second optical measurements on a sample, using one or more optical measurement devices under respective sets of measuring conditions that are different from each other;
  measuring a measurand of the sample, based upon the first optical measurement;
  measuring a measurand of the sample, based upon the second optical measurement;
  normalizing the measurand measured based upon the first optical measurement and the measurand measured based upon the second optical measurement, with respect to each other; and
  determining a parameter of the sample based upon at least one of the normalized measurand measured based upon the first optical measurement and the normalized measurand measured based upon the second optical measurement.

The present invention will be more fully understood from the following detailed description of embodiments thereof, taken together with the drawings, in which:

DETAILED DESCRIPTION OF EMBODIMENTS

Figure 1:
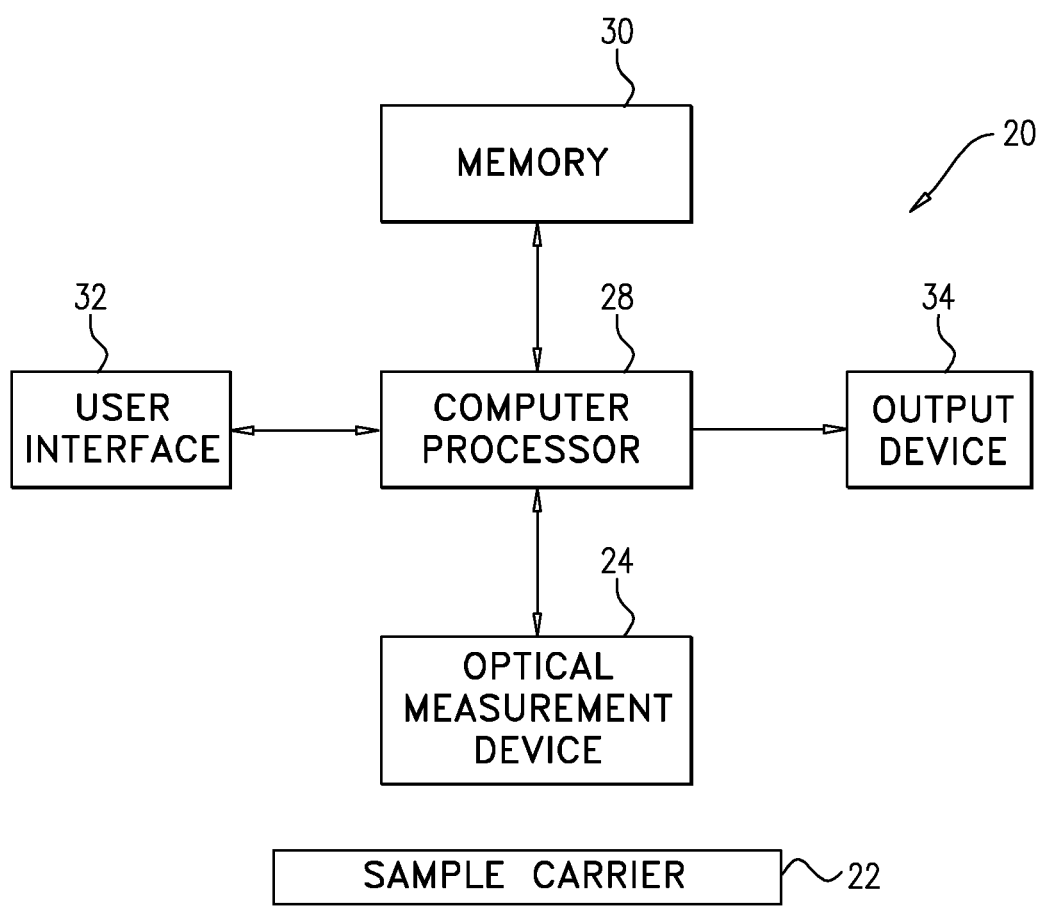
FIG. 1 is a block diagram showing components of a biological sample analysis system, in accordance some applications of the present invention.

Reference is now made to FIG. 1, which is block diagram showing components of a biological sample analysis system 20, in accordance some applications of the present invention. Typically, a biological sample (e.g., a blood sample) is placed into a sample carrier 22. While the sample is disposed in the sample carrier, optical measurements are performed upon the sample using one or more optical measurement devices 24. For example, the optical measurement devices may include a microscope (e.g., a digital microscope), a spectrophotometer, a photometer, a spectrometer, a camera, a spectral camera, a hyperspectral camera, a fluorometer, a spectrofluorometer, and/or a photodetector (such as a photodiode, a photoresistor, and/or a phototransistor). For some applications, the optical measurement devices include dedicated light sources (such as light emitting diodes, incandescent light sources, etc.) and/or optical elements for manipulating light collection and/or light emission (such as lenses, diffusers, filters, etc.). For some applications, a microscope system is used that is generally similar to the microscope system described in US 2014/0347459 to Greenfield, which is incorporated herein by reference.

A computer processor 28 typically receives and processes optical measurements that are performed by the optical measurement device. Further typically, the computer processor controls the acquisition of optical measurements that are performed by the one or more optical measurement devices. The computer processor communicates with a memory 30. A user (e.g., a laboratory technician) sends instructions to the computer processor via a user interface 32. For some applications, the user interface includes a keyboard, a mouse, a joystick, a touchscreen device (such as a smartphone or a tablet computer), a touchpad, a trackball, a voice-command interface, and/or other types of user interfaces that are known in the art. Typically, the computer processor generates an output via an output device 34. Further typically, the output device includes a display, such as a monitor, and the output includes an output that is displayed on the display. For some applications, the processor generates an output on a different type of visual, text, graphics, tactile, audio, and/or video output device, e.g., speakers, headphones, a smartphone, or a tablet computer. For some applications, user interface 32 acts as both an input interface and an output interface, i.e., it acts as an input/output interface. For some applications, the processor generates an output on a computer-readable medium (e.g., a non-transitory computer-readable medium), such as a disk, or a portable USB drive, and/or generates an output on a printer.

Figure 2:
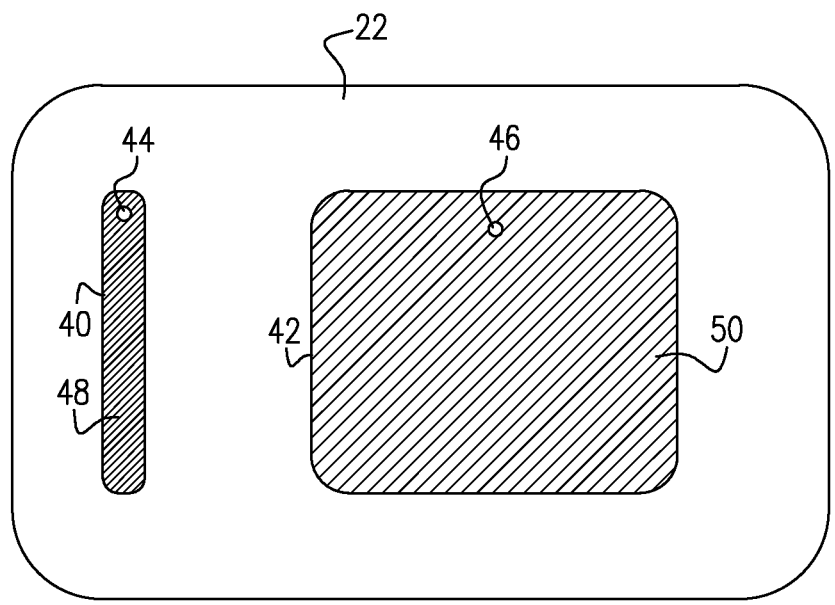
FIG. 2 is a schematic illustration of a sample carrier, in accordance with some applications of the present invention.

Reference is now made to FIG. 2, which is a schematic illustration of sample carrier 22, in accordance with some applications of the present invention. For some applications, the sample carrier includes a source sample portion chamber 40, as well as a diluted sample portion chamber 42. Typically, chambers 40 and 42 are filled via respective entry holes 44 and 46.

For some applications, diluted sample portion chamber 42 is filled with a second portion 50 of a biological sample (e.g., a portion of a blood sample), which is diluted with respect to a first portion 48 of the sample that is placed in the source sample portion chamber 40. For example, a portion of the sample may be diluted in order to identify and/or count components of the sample, which may be less easily identified and/or counted in an undiluted portion of the sample. For some applications, the diluted portion includes a staining substance. For example, a diluted portion may be prepared using techniques as described in US 2015/0316477 to Pollak, which is incorporated herein by reference, and which describes a method for preparation of blood samples for analysis that involves a dilution step, the dilution step facilitating the identification and/or counting of components within microscopic images of the sample. Typically, in such applications, although the extent of dilution is typically set as part of the protocol, small variations in the dilution can lead to corresponding errors in the absolute quantification of the different components and/or analytes within the sample. In accordance with some applications of the present invention, two different measurements are performed upon, respectively, first portion 48 of the sample that is placed in chamber 40 (i.e., a source sample portion), and second portion 50 of the sample that is placed in chamber 42, and which is diluted with respect to the first portion (i.e., a diluted sample portion). For some applications, based upon the measurements, the dilution factor (i.e., the dilution ratio, and/or the extent to which the second portion is diluted with respect to the first portion) is determined. Typically, a normalization factor is determined, the normalization factor being a property of the source sample portion to which other measurements are correlated (e.g. the number of red blood cells per unit area or per unit volume in the source sample portion). Further typically, measurands within the sample (e.g., within the source sample portion) are measured based upon the normalization factor, as described in further detail hereinbelow.

For some applications, the methods described herein are performed with respect to a source sample portion and a diluted sample portion without the portions being placed into respective chambers of a single sample carrier, as shown in FIG. 2. For some applications, the methods described herein are performed with respect to first and second portions of a sample, which are not diluted with respect to one another, mutatis mutandis. For some such applications, respective measurements (e.g., respective optical measurements) that are performed upon the first and second portions are normalized with respect to one another, using techniques as described herein.

For some applications, source sample portion 48, which is placed in the source sample portion chamber is a natural undiluted biological fluid (e.g., a blood sample or urine sample), or is a sample that underwent some modification, including, for example, one or more of dilution (e.g., dilution in a controlled fashion), addition of a component or reagent, or fractionation. Diluted sample portion 50, which is placed within the diluted sample portion chamber, is typically diluted with respect to the portion of the sample that is placed in the source sample portion chamber. For example, the diluent may contain pH buffers, stains, fluorescent stains, antibodies, sphering agents, lysing agents, etc.

Typically, an assay is performed on diluted sample portion 50 that provides a plurality of measurements, which are assumed to have good relative agreement with each other. Further typically, an assay is performed on source sample portion 48 that yields a measurement that corresponds to at least one of the measurements performed upon the diluted sample portion. For some applications, at least one of the measurements performed on diluted sample portion 50 is normalized by normalizing using measurements that are measured and/or derived from both portions 48 and 50.

For example, a blood sample may be diluted using a dilution technique as described in US 2015/0316477 to Pollak, which is incorporated herein by reference, and the smear may be suitably stained and imaged using a microscope system (which may be manual or automated). For some applications, the microscope system is one of optical measurement devices 24, described hereinabove with respect to FIG. 1. For some applications, the microscope images are analyzed (e.g. manually, or using a computer processor that runs suitable computer software) to identify different blood cells. However, an error of 10 percent in the dilution factor may correspond directly to a 10 percent error in the count of, for example, red blood cell per unit volume (e.g., per microliter) of blood. Such errors in dilution can originate from a number of sources. Illustrative examples of sources of such errors (which are not intended to limit the scope of the present invention) include pipetting inaccuracy or error, calibration inaccuracy or error, mixing inaccuracy or error, etc.

For some applications, the methods described herein are used to account for at least some of the variation in dilution by making a measurement on a source sample portion (e.g., an undiluted blood sample portion) from which the diluted sample portion is extracted. This measurement typically corresponds to at least one of the measurements measured on the diluted sample portion. For example, the measurement performed on the source sample portion may include measurement of: hemoglobin content, white blood cell content, red blood cell content, hematocrit, content of a specific white blood cell type, platelet content, and/or any measurand that is measured or that can be inferred for the diluted sample portion. For some applications, a normalization factor is determined, the normalization factor being a property of the source sample portion to which other measurements are correlated (e.g. the number of red blood cells per unit area or per unit volume in the source sample portion). Typically, measurands within the sample (e.g., within the source sample portion) are measured based upon the normalization factor, as described in further detail hereinbelow. For some applications, a plurality of measurements (for example, two or more of the above-described measurements) are performed on source sample portion 48, and a normalization factor (e.g., a dilution factor) is determined based upon the plurality of measurements. Typically, in such cases, a normalization factor is determined based upon the different components of data, using a statistical method (e.g. averaging, regression, curve-fitting or other techniques known in the art). For some applications, the accuracy of the normalization is increased by using a plurality of analytical measurements in the above-described manner, relative to if only a single measurement is used.

Typically, as described hereinabove, the above-described method is performed on two or more portions of the sample that are at different levels of dilution (i.e., a source sample portion and a dilution sample portion), whereby the amount or concentration of different components in one sample portion is determined based on a dilution factor between the two sample portions. For example, the method may be used to determine the amount or concentration of different blood components in a complete blood count assay that is conducted on a diluted blood sample portion.

For some applications, a dilution factor (i.e., the dilution ratio (such as 1:100), and/or the extent to which the second portion is diluted with respect to the first portion) is determined. For some applications, the same measurand is measured in the diluted and source sample portions. For example, a count per unit volume of a component, a concentration of a component, and/or an optical density of a component may be measured. The dilution factor for the diluted sample portion relative to the source sample portion is derived from the ratio of the measurand as measured within the two sample portions (e.g., the ratio of the count per unit volume of the component, the concentration of the component, and/or the optical density of the component as measured within the two sample portions). The dilution factor is typically used to determine a parameter relating to (e.g., the count per unit volume, the concentration, and/or the optical density of) one or more other components.

As described hereinabove, typically, a normalization factor is determined that is a property of the source sample portion to which other measurements are correlated (e.g., the number of red blood cells per unit area or per unit volume in the source sample portion). For some applications, one measurand is measured in the undiluted sample portion and a different measurand is measured in the diluted sample portion. For example, hemoglobin concentration (Hb) may be measured in a source blood sample portion, and mean corpuscular hemoglobin (MCH) may be measured in a diluted blood sample portion. Or, the hematocrit may be measured in a source blood sample portion, and mean corpuscular volume (MCV) may be measured in a diluted blood sample portion. Typically, a relationship between the two measurements is determined (e.g., the two measurements may be divided by one another), and the concentration, or count per unit volume, of a reference component in the source sample portion is inferred based upon the relationship. Thereafter, a parameter relating to (e.g., the count per unit volume, the concentration, and/or the optical density of) one or more other components is determined in correlation to a ratio of the other component with respect to the reference component. The above-described techniques will be more easily understood by means of the following examples.

For some applications (e.g., in the context of a complete blood count), a measurement is performed upon an undiluted sample to determine the total hemoglobin concentration ("Hb"), for example, using optical density measurements conducted on undiluted blood. Typically, such measurements are performed using a spectrophotometer, spectrometer, camera, a spectral camera, a hyperspectral camera, as optical measurement device 24 (FIG. 1). The mean corpuscular hemoglobin (MCH) is determined using a diluted blood sample portion. For example, optical density measurements may be performed on a cellular level (i.e., with respect to individual cells). For example, a microscope may be used as an optical measurement device 24 (FIG. 1), and cells may be imaged using bright-field imaging under violet or green wavelengths. For some applications, the red blood cell count per unit volume ("RBC") in the source sample portion is deduced by dividing the hemoglobin concentration by the mean corpuscular hemoglobin (since RBC=Hb/MCH). For some applications, based upon the red blood cell count per unit volume in the source sample portion, the count of additional components within the source sample portion is determined. For example, using a microscopic image of the diluted sample portion, the ratio of counts of other blood components (e.g. red blood cells of a given type, white blood cells, white blood cells of a given type, circulating tumor cells, platelets, platelets of a given type, bacteria, pathogens, pathogens of a given type, reticulocytes, and Howell-Jolly bodies) to the red blood cell count may be determined. Alternatively or additionally, the ratio of counts of other blood components to the red blood cell count may be determined using a microscopic image of a non-diluted sample portion, which forms a monolayer having a sufficiently low cell density for identifying individual components within the monolayer (for example, by virtue of the portion having been placed in a sample chamber having a relatively low height). The absolute count of the additional components within the source sample portion is determined by multiplying this ratio by the red blood cell count. For example, once the white blood cell to red blood cell ratio is determined in the diluted sample portion as $(WBC/RBC)_{diluted}$, the white blood cell count per unit volume in the source sample portion ("$WBC_{count}$") is calculated as $WBC_{count}=(WBC/RBC)_{diluted} \times RBC=(WBC/RBC)_{diluted} \times Hb/MCH$. For some applications, the hematocrit within the sample is determined based upon the determined red blood cell count. For example, the mean corpuscular volume may be measured with respect to the diluted sample portion, and the hematocrit may be determined by multiplying the mean corpuscular volume by the red blood cell count.

For some applications (e.g., in the context of a complete blood count), a measurement is performed upon an undiluted sample to determine the hematocrit ("HCT"), for example, using the micro-hematocrit method (in which a volume of blood is centrifuged), or using ultrasonic and/or impedance measurements. The mean corpuscular volume ("MCV") is determined using a diluted blood sample portion. For example, the red blood cells may be imaged using a microscope as optical measurement device 24 (FIG. 1), and the mean corpuscular volume may be derived from the images. For some applications, the red blood cell count per unit volume ("RBC") in the source sample portion is deduced by dividing the hematocrit by the mean corpuscular volume (since RBC=HCT/MCV). For some applications, based upon the red blood cell count per unit volume in the source sample portion, the count of additional components within the source sample portion is determined. For example, using a microscopic image of the diluted sample portion, the ratio of counts of other blood components (e.g. red blood cells of a given type, white blood cells, white blood cells of a given type, circulating tumor cells, platelets, platelets of a given type, bacteria, pathogens, pathogens of a given type, reticulocytes, and Howell-Jolly bodies) to the red blood cell count may be determined. Alternatively or additionally, the ratio of counts of other blood components to the red blood cell count may be determined using a microscopic image of a non-diluted sample portion, which forms a monolayer having a sufficiently low cell density for identifying individual components within the monolayer (for example, by virtue of the portion having been placed in a sample chamber having a relatively low height). The absolute count of the additional components within the source sample portion is determined by multiplying this ratio by the red blood cell count. For example, once the white blood cell to red blood cell ratio is determined in the diluted sample as $(WBC/RBC)_{diluted}$, the white blood cell count per unit volume in the source sample portion ("$WBC_{count}$") is calculated as $WBC_{count}=(WBC/RBC)_{diluted} \times RBC=(WBC/RBC)_{diluted} \times HCT/MCV$. For some applications, hemoglobin concentration within the sample is determined based upon the determined red blood cell count. For example, the mean corpuscular hemoglobin may be measured with respect to the diluted sample portion, and the hemoglobin concentration may be determined by multiplying the mean corpuscular hemoglobin by the red blood cell count.

For some applications (e.g., in the context of a complete blood count), the total white blood cell count per unit volume is determined in the source sample portion. For example, the total white blood cell count per unit volume may be determined by (a) lysing the red blood cells within the sample (such that the red blood cells don't cause scattering of light), (b) imaging the sample using a DNA-specific stain such as Methylene Blue, which has a high absorption in wavelengths in which the absorbance of hemoglobin from the red blood cells is low, and (c) measuring light absorption at those wavelengths. For some applications, based upon the white blood cell count per unit volume in the source sample portion, the count of additional components within the source sample portion is determined. For example, using a microscopic image of the diluted sample portion, the ratio of counts of other blood components (e.g. red blood cells, red blood cells of a given type, white blood cells of a given type, circulating tumor cells, platelets, platelets of a given type, bacteria, pathogens, pathogens of a given type, reticulocytes, and Howell-Jolly bodies) to the white blood cell count may be determined. The absolute count of the additional components within the source sample portion is determined by multiplying this ratio by the white blood cell count.

For some applications, even source sample portion 48 is not a natural biological sample, but has itself been diluted, for example. For some such applications, the counts and/or concentrations of components within the natural sample, from which the source sample portion was produced, are derived. For example, natural blood may be diluted in a controlled, precise matter to produce a source sample portion, with the dilution factor of this dilution step being precisely known. The source sample portion is then used as described hereinabove to produce diluted sample portion 50, and the count per unit volume and/or concentration of some blood components in the source sample portion is derived, as described hereinabove. Based upon the count per unit volume and/or concentration of blood components in the source sample portion, the count per unit volume and/or concentration of those components within the natural sample are derived.

For some applications, a natural sample is diluted to produce source sample portion 48, which is diluted further to produce diluted sample portion 50. Based on parameters determined for each of the source sample portion and the diluted sample portion, parameters are extrapolated for the natural sample, without directly estimating a dilution factor. For example, the ratio of white blood cells to red blood cells may be determined using microscopic images of the diluted sample portions, as described hereinabove, while the ratio of basophils to white blood cells may be determined for the source sample portion. In addition, the red blood cell count per unit volume may be determined for the natural sample. The basophils count per unit volume of the natural sample may thereby be determined, using the red blood cell count per unit volume for the natural sample in combination with the ratios.

Referring again to FIG. 2, for some applications, the techniques described herein are performed using carrier 22, the carrier having at least two chambers for each patient (or source), as described hereinabove. Typically, source sample portion chamber 40 is configured to assay a small volume, such as between 1 microliter and 30 microliters of blood, so as not to necessitate, for example, drawing much blood. Further typically, the source sample portion chamber and diluted sample portion chamber are in close proximity to one another, for example by being disposed upon a single sample carrier, as shown in FIG. 2. For some applications, the proximity of the source and diluted sample chambers to one another is beneficial in reducing the hazard of mismatching a source sample and a diluted sample.

As described hereinabove, for some applications, the methods described herein are performed with respect to a source sample portion and a diluted sample portion without the portions being placed into respective chambers of a single sample carrier, as shown in FIG. 2. For some applications, the methods described herein are performed with respect to first and second portions of a sample, which are not diluted with respect to one another, mutatis mutandis. For such applications, respective measurements (e.g., respective optical measurements) that are performed upon the first and second portions are normalized with respect to one another, using techniques as described herein.

Although some of the above examples are described with reference to performing certain measurements with respect to source and diluted sample portions of a blood sample, the scope of the present invention includes generally performing combinations of measurements (e.g., optical measurements) on a sample (and/or portions thereof), to thereby derive a parameter of the sample, as described with reference to the flowcharts shown in FIGS. 3-7.

Figure 3:
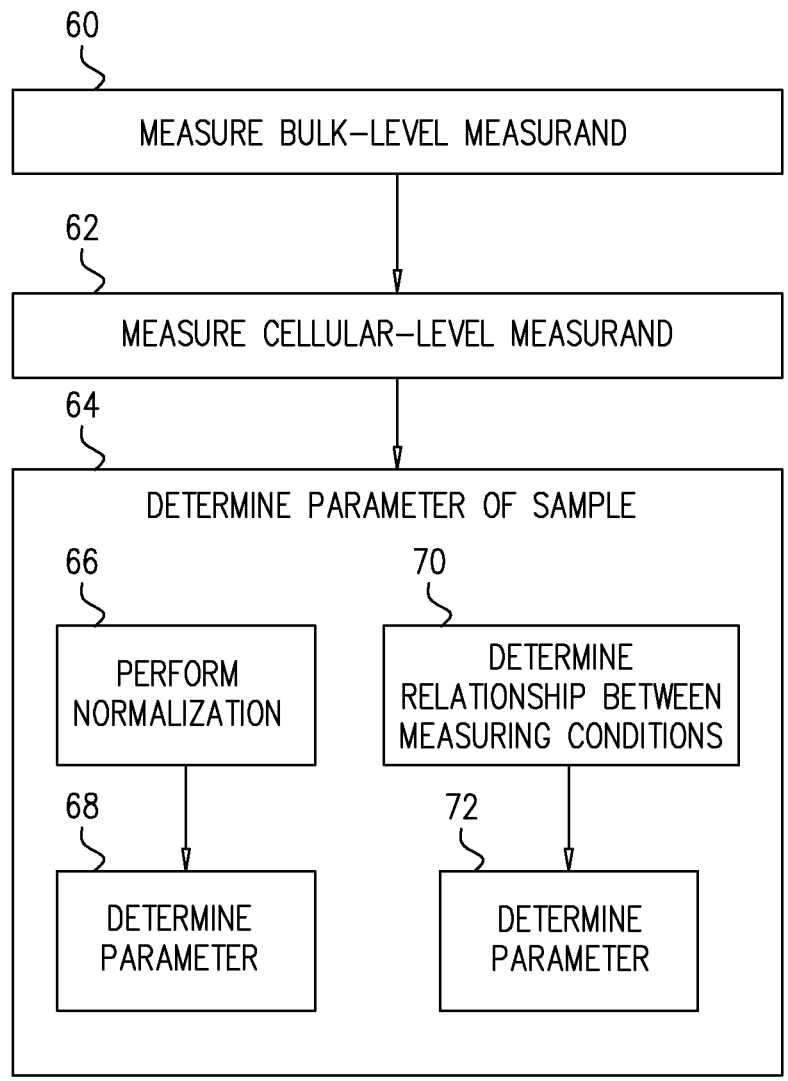
FIG. 3 is a flowchart showing steps of algorithm that is performed, in accordance with some applications of the present invention.

Reference is now made to FIG. 3, which is a flowchart showing steps of algorithm that is performed, in accordance with some applications of the present invention. In accordance with some applications of the present invention, two or more measurements (which are typically optical measurements) are performed upon a biological sample. Typically, the biological sample is a blood sample. For some applications, a bulk-level measurand of the sample is measured, by performing a first measurement on the sample, in a first step 60. Further typically, a cellular-level measurand of the sample is measured, by performing a second measurement on the sample, in a second step 62. For the purpose of the present applications, the term "cellular-level measurand" should be understood to mean a measurand that relates to one or more parameters of individual cells or other non-dissolved components within the sample, such as mean corpuscular volume, mean corpuscular hemoglobin, mean platelet volume, and/or red blood cell distribution width, etc. Measurement of a cellular-level measurand typically involves a first step of identifying individual cells or other non-dissolved components within the sample (e.g., identifying such components within a microscopic image), and a second step of identifying a parameter of such individual identified components. For some applications, the cellular-level measurand is measured by analyzing one or more microscopic images of the sample. For the purpose of the present applications, the term "bulk-level measurand" should be understood to mean a measurand that relates a parameter of the sample as a whole, and that does not require the two steps of identifying individual cells or other non-dissolved components within the sample, and identifying a parameter of such individual identified components. For example, such a measurand may include the optical density of a given component (which is measured by performing a measurement on a bulk volume of the sample, e.g., even after performing lysis of individual components within the bulk volume), a count per unit volume of a given component (which is typically measured by identifying such components, but does not require identifying a parameter of individual identified components), and/or the concentration of a given component (such as red blood cell concentration, hemoglobin concentration, white blood cell concentration, platelet concentration, and/or hematocrit, i.e., red blood cell concentration). Typically, bulk-level measurands are measured by performing a measurement on a bulk volume of the sample. For example, such measurements may include ultrasonic, impedance, optical absorption, transmittance, fluorescence, microscopic and/or luminescence measurements that are performed on a bulk volume of the sample. In accordance with respective applications, the first and second measurements are performed on the same portion of the sample, or on respective, different portions of the sample.

Typically, in a third step 64, a parameter of the sample is determined, based on a relationship between the bulk-level measurand and the cellular-level measurand. For some applications, in a sub-step 66 of step 64, the first measurement is normalized with respect to the second measurement. Typically, a relationship between the two measurements is determined (e.g., the two measurements may be divided by one another), and the concentration, or count per unit volume, of a reference component is inferred based upon the relationship, as described hereinabove. For some applications, the second measurement is performed on a second portion of the sample that is diluted with respect to a first portion of the sample upon which the first measurement is performed, and in sub-step 66, a dilution ratio by which the second portion of the sample is diluted with respect to the first portion of the sample is determined. For some applications, in a further sub-step 68 of step 64, the parameter of the sample is determined, based upon the normalization, and a further measurement that is performed on the sample, as described in further detail herein.

For some applications, the first measurement is performed using a first set of measuring conditions, and the second measurement is performed using a second set of measuring conditions. For some such applications, in a sub-step 70 of step 64, a relationship between the sets of measuring conditions is determined. Typically, in a further sub-step 72, a parameter of the sample is determined based upon the relationship between the sets of measuring conditions. For example, the first and second optical measurements may be performed on respective portions of the sample that are disposed in respective portions of one or more sample chambers having respective dimensions (e.g., respective heights). For some such applications, a relationship between dimensions of the respective portions of the one or more sample chambers is determined, based on the relationship between the bulk-level measurand and the cellular-level measurand. Alternatively or additionally, a field of view from which one of the first and second optical measurements was measured (e.g., a microscopic image was acquired) is determined, and/or a level of magnification at which one of the first and second optical measurements was measured (e.g., a microscopic image was acquired) is determined. For some applications, the bulk-level measurand and the cellular-level measurand are normalized with respect to one another. Subsequently, a parameter of the sample is determined based upon the normalization of the bulk-level measurand and the cellular-level measurand with respect to one another.

Figure 4:
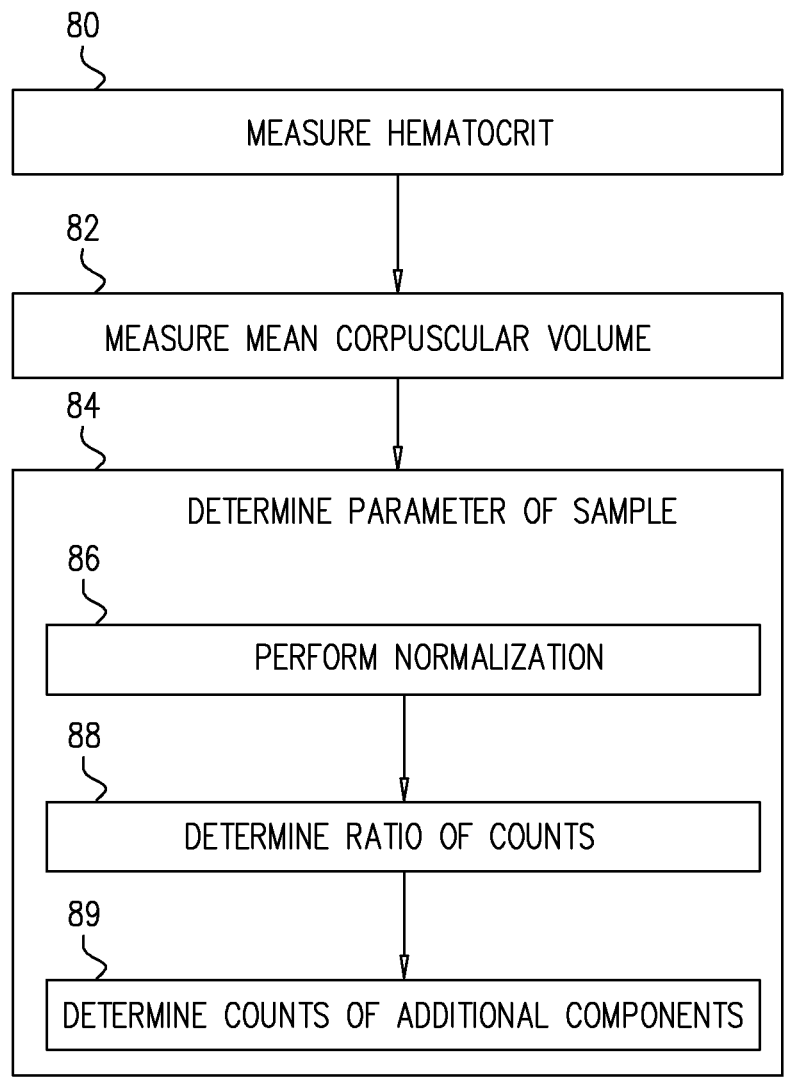
FIG. 4 is a flowchart showing steps of algorithm that is performed, in accordance with some applications of the present invention.

Reference is now made to FIG. 4, which is a flowchart showing steps of algorithm that is performed, in accordance with some applications of the present invention. For some applications, in a first step 80, hematocrit is measured by performing a first measurement on a blood sample, and, in a second step 82, mean corpuscular volume within the blood sample is measured, by performing a second measurement on the blood sample. For example, hematocrit may be measured using the micro-hematocrit method, or using ultrasonic and/or impedance measurements, and the mean corpuscular volume may be measured by analyzing microscopic images that are acquired of a second portion of the blood sample. Typically, the second portion of the sample is diluted with respect to the first portion of the blood sample.

Typically, in a third step 84, a parameter of the sample is determined based upon the relationship between the hematocrit and the mean corpuscular volume. For some applications, in a sub-step 86 of step 84, based on the relationship between the hematocrit and the mean corpuscular volume, the first portion of the sample and second portion of the sample are normalized with respect to each other. Typically, the red blood cell count (e.g., count per unit volume) within the sample is determined by dividing the hematocrit by the mean corpuscular volume, such that the red blood cell count can thereby act as a reference parameter with reference to which other parameters are normalized. For some applications, counts of one or more additional components within the sample (e.g., red blood cells of a given type, white blood cells, white blood cells of a given type, circulating tumor cells, platelets, platelets of a given type, bacteria, pathogens, pathogens of a given type, reticulocytes, and/or Howell-Jolly bodies) are determined, based on the red blood cell count within the sample. For example, in a sub-step 88 of step 84, a ratio between the red blood cell count and the counts of the one or more additional components within a portion of the sample may be determined, by analyzing a microscopic image of the diluted portion of the sample. Subsequently, in a sub-step 89 of step 84, the counts of the one or more additional components are determined, based on the red blood cell count within the source sample portion and the ratio between the red blood cell count and the counts of the one or more additional components within the diluted portion of the sample.

Figure 5:
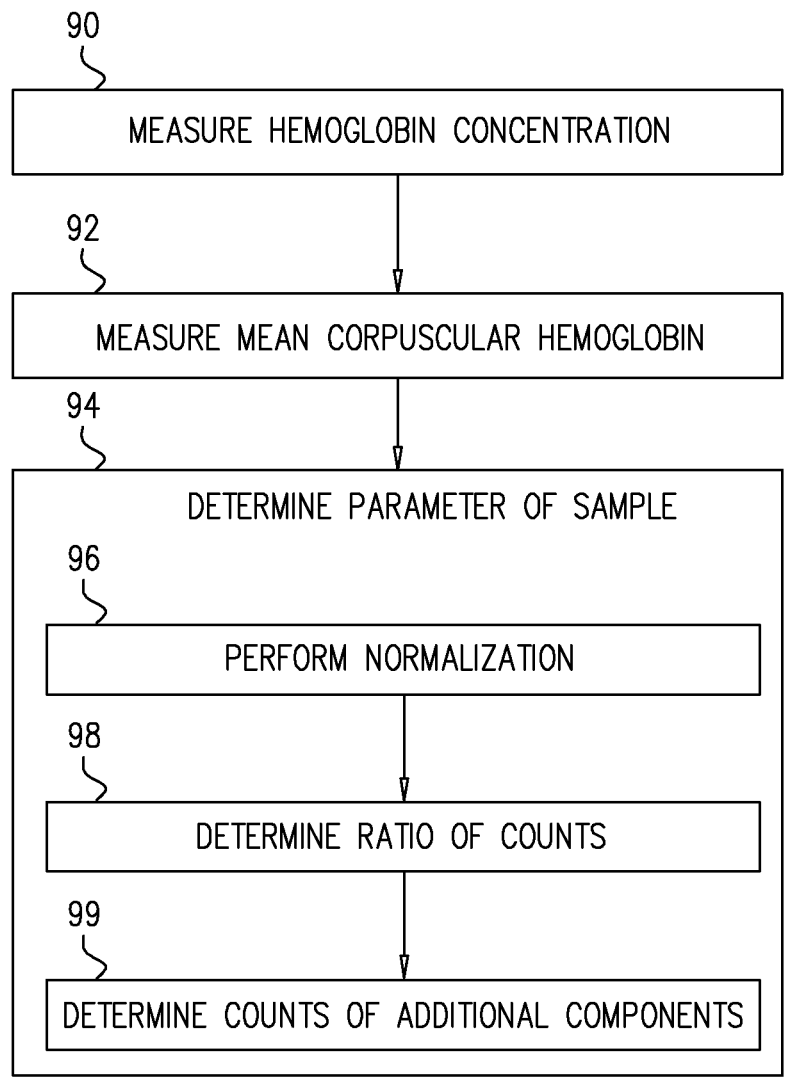
FIG. 5 is a flowchart showing steps of algorithm that is performed, in accordance with some applications of the present invention.

Reference is now made to FIG. 5, which is a flowchart showing steps of algorithm that is performed, in accordance with some applications of the present invention. For some applications, in a first step 90, hemoglobin concentration is measured by performing a first measurement on a blood sample, and, in a second step 92, mean corpuscular hemoglobin within the blood sample is measured, by performing a second measurement on the blood sample. For example, hemoglobin concentration may be measured by performing optical density measurements on a first portion of the blood sample, and the mean corpuscular hemoglobin may be measured by performing optical density measurements on a cellular level (i.e., with respect to individual cells) on a second portion of the sample. Typically, the second portion of the sample is diluted with respect to the first portion of the blood sample.

Typically, in a third step 94, a parameter of the sample is determined based upon the relationship between the hemoglobin concentration and the mean corpuscular hemoglobin. For some applications, in a sub-step 96 of step 94, based on the relationship between the hemoglobin concentration and the mean corpuscular hemoglobin, the first portion of the sample and second portion of the sample are normalized with respect to each other. Typically, the red blood cell count (e.g., count per unit volume) within the sample is determined by dividing the hemoglobin concentration and the mean corpuscular hemoglobin, such that the red blood cell count can thereby act as a reference parameter with reference to which other parameters are normalized. For some applications, counts of one or more additional components within the sample (e.g., red blood cells of a given type, white blood cells, white blood cells of a given type, circulating tumor cells, platelets, platelets of a given type, bacteria, pathogens, pathogens of a given type, reticulocytes, and/or Howell-Jolly bodies) are determined, based on the red blood cell count within the sample. For example, in a sub-step 98 of step 94, a ratio between the red blood cell count and the counts of the one or more additional components within the diluted portion of the sample may be determined, by analyzing a microscopic image of the portion of the diluted portion of the sample. Subsequently, in a sub-step 99 of step 94, the counts of the one or more additional components are determined, based on the red blood cell count within the source sample portion and the ratio between the red blood cell count and the counts of the one or more additional components within the diluted portion of the sample.

Figure 6:
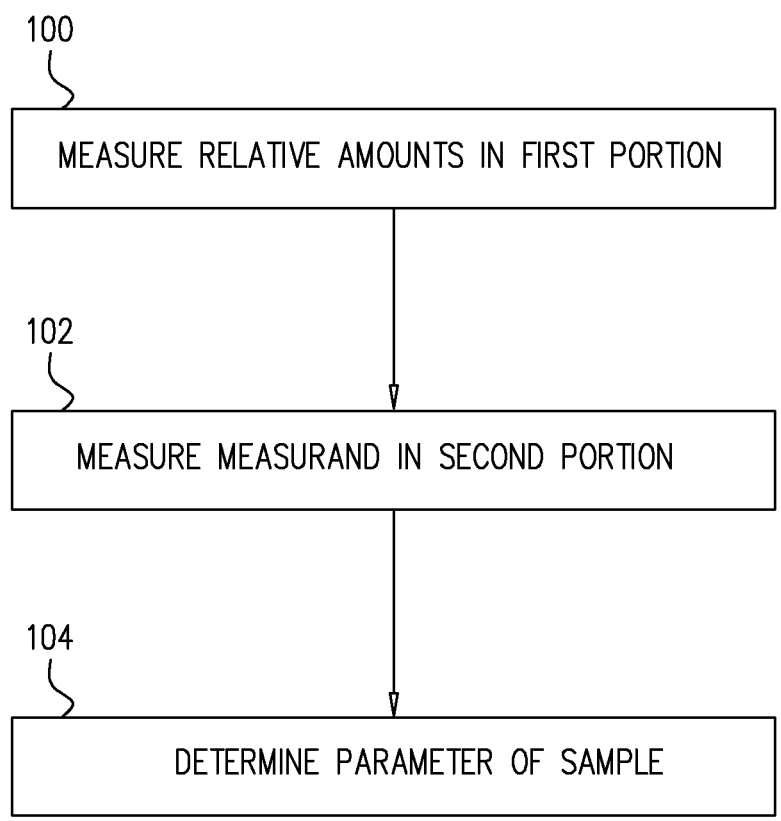
FIG. 6 is a flowchart showing steps of algorithm that is performed, in accordance with some applications of the present invention.

Reference is now made to FIG. 6, which is a flowchart showing steps of algorithm that is performed, in accordance with some applications of the present invention. For some applications, in a first step 100, relative amounts of first and second components are measured within the first portion of the blood sample. In a second step 102, a measurand is measured within a second portion of the blood sample. In a third step 104, a parameter of the blood sample is determined based upon a relationship between the relative amounts of first and second components within the first portion of the blood sample, and the measurand within the second portion of the blood sample. For some applications, the steps described in the flowchart shown in FIG. 6 are performed in combination with steps shown in any one of the other flowcharts.

Typically, step 100 is performed by analyzing a microscopic image of the first portion of the blood sample. For some applications, the first portion is diluted with respect to the second portion, e.g., as described hereinabove. (It is noted that the diluted and source portions of the sample are described interchangeably as first and second portions of the sample.)

For some applications, in step 100, relative amounts of all white blood cell types, neutrophils, eosinophils, basophils, lymphocytes, monocytes, and/or white blood cell precursors are measured, e.g., by analyzing a microscopic image of the first portion of the blood sample. In step 102, the absolute count of all types of white blood cells is determined. For some applications, step 102 is performed by performing a bulk-level measurement, e.g., by performing an optical density measurement upon a source sample portion. In step 104, the absolute counts of respective types of white blood cells (or of a given type of white blood cell) is determined, based upon steps 100 and 102.

For some applications, in step 100, relative amounts of red blood cells, reticulocytes, intracellular bodies, red blood cells having a given morphology, and/or Howell-Jolly bodies are measured, e.g., by analyzing a microscopic image of the first portion of the blood sample. In step 102, the absolute count of all types of the above-described components is determined, e.g., by performing an optical density measurement upon a source sample portion. In step 104, the absolute counts of respective types of the above-described components (or of a given one of the above-described components) is determined, based upon steps 100 and 102.

For some applications, in step 100, relative amounts of reticulocyted platelets, giant platelets, and/or regular platelets are measured, e.g., by analyzing a microscopic image of the first portion of the blood sample. In step 102, the absolute count of all platelet types is determined, e.g., by performing an optical density measurement upon a source sample portion. In step 104, the absolute counts of respective types of platelets (or of a given type of platelet) is determined, based upon steps 100 and 102.

For some applications, combinations of different cell types are analyzed using the technique described with reference to FIG. 6. For example, ratios of any combination of red blood cells, red blood cells of given types, white blood cells, white blood cells of given types, platelets, platelets of given types, intracellular bodies, precursor cells, circulating tumor cells, pathogens, pathogens of a given type, reticulocytes, and/or Howell-Jolly bodies, etc. may be measured in the first portion, and in the second portion absolute counts of any of the aforementioned components may be measured, such as to derive an absolute count of another one of the components, mutatis mutandis.

Figure 7:
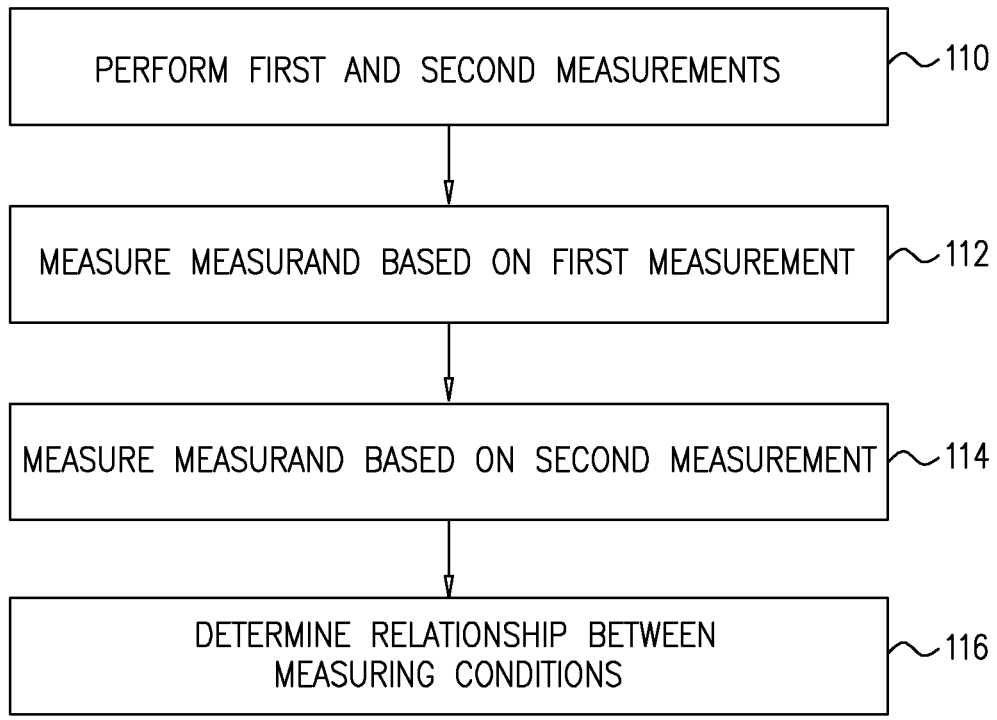
FIG. 7 is a flowchart showing steps of algorithm that is performed in accordance with some applications of the present invention.

Reference is now made to FIG. 7, which is a flowchart showing steps of algorithm that is performed, in accordance with some applications of the present invention. For some applications, in a first step 110, first and second optical measurements are performed on a sample, using one or more optical measurement devices under respective sets of measuring conditions that are different from each other. Typically, in a second step 112, a measurand of the sample is measured, based upon the first optical measurement, and, in a third step 114, a measurand of the sample is measured, based upon the second optical measurement. In accordance with respective applications, the measurand that is measured based upon the second optical measurement is the same as the measurand that is measured based upon the first optical measurement, or is different from the measurand that is measured based upon the first optical measurement. In accordance with respective applications, the first and second optical measurements are performed on the same portion of the sample, or on different portions of the sample. For some applications, one of the optical measurements is performed on a portion of the sample that is diluted with respect to a portion of the sample upon which the other optical measurement is performed.

Typically, in a fourth step 116, based on a relationship between the measurand measured based upon the first optical measurement and the measurand measured based upon the second optical measurement, a relationship between the measuring conditions of the one or more optical measurement devices that were used to perform the first and second optical measurements is determined. For example, a field of view from which one of the first and second optical measurements was measured (e.g., a microscopic image was acquired) is determined, and/or a level of magnification at which one of the first and second optical measurements was measured (e.g., a microscopic image was acquired) is determined. For some applications, the first and second optical measurements are normalized with respect to one another, and a parameter of the sample is determined based upon the normalized measurements, e.g., using techniques described herein.

For some applications, the first measurement is performed using a first type of optical measurement device (e.g., a device configured to perform cellular-level measurements, such as a microscope), and the second measurement is performed using a second type of optical measurement device (e.g., a device configured to perform bulk-level measurements, such as a spectrophotometer, a photometer, a spectrometer, a camera, a spectral camera, a hyperspectral camera, a fluorometer, a spectrofluorometer, and/or a photodetector). Measurements using the respective types of devices are normalized with respect to each other, such as to account for errors and/or inaccuracies in one or both of the devices. For example, the normalization may account for errors in the level of magnification of a microscope, and/or the gain of a device configured to perform bulk-level measurements, such as a spectrophotometer, a photometer, a spectrometer, a camera, a spectral camera, a hyperspectral camera, a fluorometer, a spectrofluorometer, and/or a photodetector.

Figure 8:
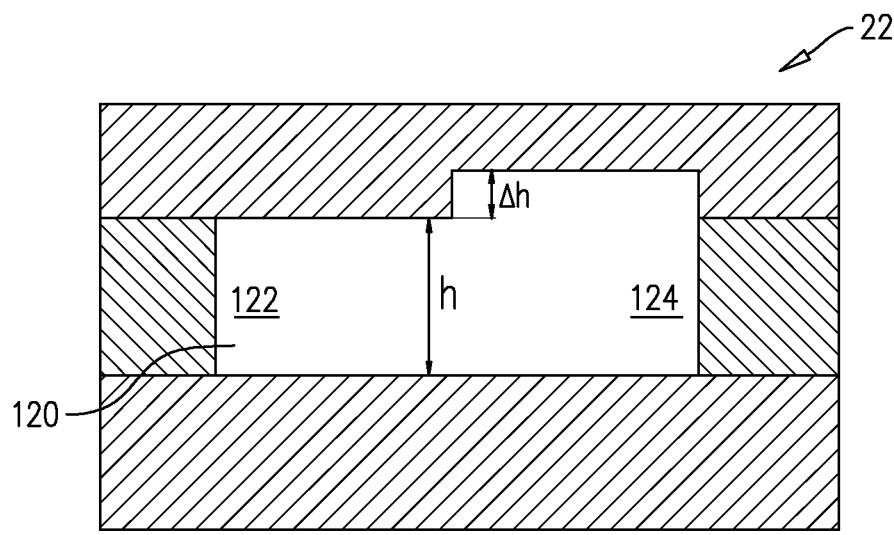
FIG. 8 is a schematic cross-sectional illustration of a sample carrier that defines a variation in height that is stepped, in accordance with some applications of the present invention.

Reference is now made to FIG. 8, which is a schematic cross-sectional illustration of sample carrier 22, in accordance with some applications of the present invention. For some applications, the sample carrier defines one or more sample chambers 120, into which the sample is placed, and the one or more sample chambers define at least a first region 122 (which is shallower) and a second region 124 (which is deeper), the height of the one or more sample chambers varying between the first and second regions. (For example, as shown, the height of the first region is h, and the height of the second region is (h+Δh).) For some applications, a first optical measurement is performed on a first portion of the sample, which is disposed within the first region, and a second optical measurement is performed on a second portion of the sample, which is disposed in the second region. For example, such measurements may be performed in accordance with techniques described in an International application being filed on even date herewith, entitled "Sample carrier for optical measurements," which is incorporated herein by reference. For some such applications, a technique as described with respect to FIG. 7 is performed, in which, in step 116, the relationship between the heights of the respective portions of the one or more sample chambers is determined, based on the relationship between the measurand measured based upon the first optical measurement and the measurand measured based upon the second optical measurement.

It is noted with reference to the flowcharts shown in FIGS. 3-7 that the steps of the flowchart are not necessarily performed in the order in which they appear in the flowcharts. For some applications, steps of the flowcharts shown in FIGS. 3-7 are performed in combination with one another. It is further noted that, in general, in response to the parameters of the sample that are determined using the techniques described herein, an output is generated, e.g., via user interface 32, and/or output device 34, both of which are shown in FIG. 1.

For some applications, the sample as described herein is a sample that includes blood or components thereof (e.g., a diluted or non-diluted whole blood sample, a sample including predominantly red blood cells, or a diluted sample including predominantly red blood cells), and parameters are determined relating to components in the blood such as platelets, white blood cells, anomalous white blood cells, circulating tumor cells, red blood cells, reticulocytes, Howell-Jolly bodies, etc.

Although some applications of the present invention have been described with reference to performing a complete blood count, and/or with respect to the analysis of blood in general, the scope of the present invention includes using the techniques described herein to perform other types of analysis, mutatis mutandis. For example, the techniques described herein may be applied to methods related to quantifying blood cells and/or other analytes in blood, methods for analyzing urine (e.g. for cell clumps), cerebral-spinal fluid (CSF), gynecological samples, fecal samples, synovial fluid samples, saliva, semen, sweat, sputum, vaginal fluid, breast milk, bronchoalveolar lavage, gastric lavage, tears, nasal discharge, biological excretions or other biological samples originating from humans or other species. The techniques are not limited to the counting of cells and can be used for the quantification of other analytes such as proteins, peptides, small molecules, infectious agents, etc. The biological sample may be from any living creature, and is typically from warm blooded animals. For some applications, the biological sample is a sample from a mammal, e.g., from a human body. For some applications, the sample is taken from any domestic animal, zoo animals and farm animals, including but not limited to dogs, cats, horses, cows and sheep. Alternatively or additionally, the biological sample is taken from animals that act as disease vectors including deer or rats.

For some applications, similar techniques to those described hereinabove are applied to a non-bodily sample. For some applications, the sample is an environmental sample, such as, a water (e.g. groundwater) sample, surface swab, soil sample, air sample, or any combination thereof. In some embodiments, the sample is a food sample, such as, a meat sample, dairy sample, water sample, wash-liquid sample, beverage sample, and any combination thereof. For some applications, the techniques described herein are applied to the analysis of non-biological substances, such as the analysis of analytes in an industrial setting.

Applications of the invention described herein can take the form of a computer program product accessible from a computer-usable or computer-readable medium (e.g., a non-transitory computer-readable medium) providing program code for use by or in connection with a computer or any instruction execution system, such as computer processor 28. For the purpose of this description, a computer-usable or computer readable medium can be any apparatus that can comprise, store, communicate, propagate, or transport the program for use by or in connection with the instruction execution system, apparatus, or device. The medium can be an electronic, magnetic, optical, electromagnetic, infrared, or semiconductor system (or apparatus or device) or a propagation medium. Typically, the computer-usable or computer readable medium is a non-transitory computer-usable or computer readable medium.

Examples of a computer-readable medium include a semiconductor or solid state memory, magnetic tape, a removable computer diskette, a random-access memory (RAM), a read-only memory (ROM), a rigid magnetic disk and an optical disk. Current examples of optical disks include compact disk-read only memory (CD-ROM), compact disk-read/write (CD-R/W) and DVD.

A data processing system suitable for storing and/or executing program code will include at least one processor (e.g., computer processor 28) coupled directly or indirectly to memory elements (e.g., memory 30) through a system bus. The memory elements can include local memory employed during actual execution of the program code, bulk storage, and cache memories which provide temporary storage of at least some program code in order to reduce the number of times code must be retrieved from bulk storage during execution. The system can read the inventive instructions on the program storage devices and follow these instructions to execute the methodology of the embodiments of the invention.

Network adapters may be coupled to the processor to enable the processor to become coupled to other processors or remote printers or storage devices through intervening private or public networks. Modems, cable modem and Ethernet cards are just a few of the currently available types of network adapters.

Computer program code for carrying out operations of the present invention may be written in any combination of one or more programming languages, including an object-oriented programming language such as Java, Smalltalk, C++ or the like and conventional procedural programming languages, such as the C programming language or similar programming languages.

It will be understood that blocks of the flowcharts shown in FIGS. 3, 4, 5, 6, and 7, and combinations of blocks in the flowcharts, can be implemented by computer program instructions. These computer program instructions may be provided to a processor of a general-purpose computer, special purpose computer, or other programmable data processing apparatus to produce a machine, such that the instructions, which execute via the processor of the computer (e.g., computer processor 28) or other programmable data processing apparatus, create means for implementing the functions/acts specified in the flowcharts and/or algorithms described in the present application. These computer program instructions may also be stored in a computer-readable medium (e.g., a non-transitory computer-readable medium) that can direct a computer or other programmable data processing apparatus to function in a particular manner, such that the instructions stored in the computer-readable medium produce an article of manufacture including instruction means which implement the function/act specified in the flowchart blocks and algorithms. The computer program instructions may also be loaded onto a computer or other programmable data processing apparatus to cause a series of operational steps to be performed on the computer or other programmable apparatus to produce a computer implemented process such that the instructions which execute on the computer or other programmable apparatus provide processes for implementing the functions/acts specified in the flowcharts and/or algorithms described in the present application.

Computer processor 28 is typically a hardware device programmed with computer program instructions to produce a special purpose computer. For example, when programmed to perform the algorithms described with reference to FIGS. 3, 4, 5, 6, and 7, computer processor 28 typically acts as a special purpose sample-analysis computer processor. Typically, the operations described herein that are performed by computer processor 28 transform the physical state of memory 30, which is a real physical article, to have a different magnetic polarity, electrical charge, or the like depending on the technology of the memory that is used.

The apparatus and methods described herein may be used in conjunction with apparatus and methods described in any one of the following patent applications, all of which are incorporated herein by reference:

US 2012/0169863 to Bachelet;
US 2014/0347459 to Greenfield;
US 2015/0037806 to Pollak;
US 20150316477 to Pollak;
US 20160208306 to Pollak;
US 20160246046 to Yorav Raphael;
US 20160279633 to Bachelet;
WO 16/030897 to Yorav Raphael;
WO 17/046799 to Eshel; and
WO 17/168411 to Eshel.

There is provided, in accordance with some applications of the present invention, the following inventive concepts:

1. A method for use with a biological sample, the method comprising:
    measuring a bulk-level measurand of the sample, by performing a first measurement on the sample;
    measuring a cellular-level measurand of the sample, by performing a second measurement on the sample; and
    determining a parameter of the sample, based on a relationship between the bulk-level measurand and the cellular-level measurand.

2. The method according to inventive concept 1, wherein determining the parameter of the blood sample comprises normalizing the first and second measurements with respect to each other, based on the relationship between the bulk-level measurand and the cellular-level measurand.

3. The method according to inventive concept 1, wherein measuring the bulk-level measurand comprises determining an optical density of a given component within the sample.

4. The method according to inventive concept 1, wherein measuring the cellular-level measurand comprises analyzing a microscopic image of the sample.

5. The method according to inventive concept 1, wherein performing the first measurement on the sample comprises performing the first measurement on the sample using a first set of measuring conditions, wherein performing the second measurement on the sample comprises performing the second measurement on the sample using a second set of measuring conditions, and wherein determining the parameter of the sample comprises determining a relationship between the measuring conditions that were used to perform the first and second measurements, based on the relationship between the bulk-level measurand and the cellular-level measurand.

6. The method according to inventive concept 1, wherein performing the first measurement comprises performing the first measurement on a first portion of the sample, and wherein performing the second measurement comprises performing the second measurement upon the first portion of the sample.

7. The method according to any one of inventive concepts 1-5, wherein performing the first measurement comprises performing the first measurement on a first portion of the sample, and wherein performing the second measurement comprises performing the second measurement upon a second portion of the sample that is different from the first portion of the sample.

8. The method according to inventive concept 7, wherein determining the parameter of the sample comprises determining a relationship between the first portion of the sample and second portion of the sample, based on the relationship between the bulk-level measurand and the cellular-level measurand.

9. The method according to inventive concept 7, wherein performing the second measurement upon the second portion of the sample comprises performing the second measurement upon a second portion of the sample that is diluted with respect to the first portion of the sample.

10. The method according to inventive concept 9, wherein determining the parameter of the sample comprises determining a normalization factor by determining a property of the first portion of the sample portion for using as a reference to which measurements within the second portion can be correlated.

11. The method according to inventive concept 9, wherein determining the parameter of the sample comprises determining a dilution ratio by which the second portion of the sample is diluted with respect to the first portion of the sample.

12. The method according to any one of inventive concepts 1-6, wherein the biological sample includes a blood sample, and wherein determining the parameter of the sample comprises determining a parameter of the blood sample.

13. The method according to inventive concept 12, wherein:
measuring the bulk-level measurand of the sample comprises measuring hematocrit of the blood sample;
measuring the cellular-level measurand of the sample comprises measuring mean corpuscular volume of the blood sample; and
determining the parameter of the sample comprises determining the parameter of the sample, based on a relationship between the hematocrit and the mean corpuscular volume.

14. The method according to inventive concept 12, wherein:
measuring the bulk-level measurand of the sample comprises measuring hemoglobin concentration within at least a portion of the blood sample;
measuring the cellular-level measurand of the sample comprises measuring mean corpuscular hemoglobin of the blood sample; and
determining the parameter of the sample comprises determining the parameter of the sample, based on a relationship between the hemoglobin concentration and the mean corpuscular hemoglobin.

15. Apparatus for use with a biological sample, the apparatus comprising:
at least one computer processor configured to:
measure a bulk-level measurand of the sample, by performing a first measurement on the sample,
measure a cellular-level measurand of the sample, by performing a second measurement on the sample, and
determine a parameter of the sample, based on a relationship between the bulk-level measurand and the cellular-level measurand.

16. A computer software product, for use with a biological sample, the computer software product comprising a non-transitory computer-readable medium in which program instructions are stored, which instructions, when read by a computer cause the computer to perform the steps of:
measuring a bulk-level measurand of the sample, by performing a first measurement on the sample;
measuring a cellular-level measurand of the sample, by performing a second measurement on the sample; and
determining a parameter of the sample, based on a relationship between the bulk-level measurand and the cellular-level measurand.

17. A method for use with a biological sample, the method comprising:
performing first and second optical measurements on the sample, using one or more optical measurement devices under respective sets of measuring conditions that are different from each other;
measuring a measurand of the sample, based upon the first optical measurement;
measuring a measurand of the sample, based upon the second optical measurement; and
based on a relationship between the measurand measured based upon the first optical measurement and the measurand measured based upon the second optical measurement, determining a relationship between the measuring conditions of the one or more optical measurement devices that were used to perform the first and second optical measurements.

18. The method according to inventive concept 17, wherein the biological sample includes a blood sample, and wherein performing first and second optical measurements on the sample comprises performing first and second optical measurements on the blood sample.

19. The method according to inventive concept 17, wherein:
performing first and second optical measurements on a sample comprises performing first and second optical measurements on respective portions of the sample that are disposed in respective portions of one or more sample chambers having respective dimensions; and
determining the relationship between the measuring conditions of the one or more optical measurement devices that were used to perform the first and second optical measurements comprises determining a relationship between dimensions of the respective portions of the one or more sample chambers.

20. The method according to inventive concept 17, wherein performing the first and second optical measurements on the sample comprises performing at least one of the first and second optical measurements by acquiring an image of at least a portion of the sample, and wherein determining the relationship between the measuring conditions of the one or more optical measurement devices that were used to perform the first and second optical measurements comprises determining a field of view of the image.

21. The method according to inventive concept 17, wherein performing the first and second optical measurements on the sample comprises performing at least one of the first and second optical measurements by acquiring an image of at least a portion of the sample, and wherein determining the relationship between the measuring conditions of the one or more optical measurement devices that were used to perform the first and second optical measurements comprises determining a level of magnification of the image.

22. The method according to inventive concept 17, wherein:
  measuring the measurand of the sample, based upon the first optical measurement comprises measuring a given measurand of the sample, based upon the first optical measurement;
  measuring the measurand of the sample, based upon the second optical measurement comprises measuring the same given measurand of the sample, based upon the second optical measurement; and
  determining the relationship between the measuring conditions of the one or more optical measurement devices that were used to perform the first and second optical measurements comprises determining the relationship between the measuring conditions of the one or more optical measurement devices that were used to perform the first and second optical measurements, based upon a relationship the given measurand as measured based upon the first optical measurement, and the given measurand as measured based upon the second optical measurement.

23. The method according to inventive concept 17, wherein performing the first optical measurement comprises performing the first optical measurement using a given optical measurement device, and performing the second optical measurement comprises performing the second optical measurement using the same given optical measurement device.

24. The method according to any one of inventive concepts 17-22, wherein performing the first optical measurement comprises performing the first optical measurement using a first optical measurement device, and performing the second optical measurement comprises performing the second optical measurement using a second optical measurement device that is different from the first optical measurement device.

25. The method according to inventive concept 24, wherein:
  performing the first optical measurement comprises performing the first optical measurement using a first optical measurement device that is configured to measure a parameter of one or more components within the sample, the parameter being selected from the group consisting of: optical absorption, transmittance, fluorescence, and luminescence; and
  performing the second optical measurement comprises performing the second optical measurement using a microscope configured to acquire a microscopic image of the sample.

26. The method according to any one of inventive concepts 17-21 or 23, wherein:
  measuring the measurand of the sample, based upon the first optical measurement comprises measuring a first measurand of the sample, based upon the first optical measurement; and
  measuring the measurand of the sample, based upon the second optical measurement comprises measuring a second measurand of the sample that is different from the first measurand, based upon the second optical measurement; and determining the relationship between the measuring conditions of the one or more optical measurement devices that were used to perform the first and second optical measurements comprises determining the relationship between the measuring conditions of the one or more optical measurement devices that were used to perform the first and second optical measurements, based upon a relationship between the first and second measurands.

27. The method according to inventive concept 26, wherein measuring the first measurand comprises measuring a bulk-level measurand of the sample, and measuring the second measurand comprises measuring a cellular-level measurand of the sample.

28. Apparatus for use with a biological sample, the apparatus comprising:
  at least one computer processor configured to:
    perform first and second optical measurements on the sample, using one or more optical measurement devices under respective sets of measuring conditions that are different from each other,
    measure a measurand of the sample, based upon the first optical measurement,
    measure a measurand of the sample, based upon the second optical measurement, and
    based on a relationship between the measurand measured based upon the first optical measurement and the measurand measured based upon the second optical measurement, determine a relationship between the measuring conditions of the one or more optical measurement devices that were used to perform the first and second optical measurements.

29. A computer software product, for use with a biological sample, the computer software product comprising a non-transitory computer-readable medium in which program instructions are stored, which instructions, when read by a computer cause the computer to perform the steps of:
  performing first and second optical measurements on a sample, using one or more optical measurement devices under respective sets of measuring conditions that are different from each other;
  measuring a measurand of the sample, based upon the first optical measurement;
  measuring a measurand of the sample, based upon the second optical measurement; and
  based on a relationship between the measurand measured based upon the first optical measurement and the measurand measured based upon the second optical measurement, determining a relationship between the measuring conditions of the one or more optical measurement devices that were used to perform the first and second optical measurements.

30. A method for use with a biological sample, the method comprising:
  performing first and second optical measurements on the sample, using one or more optical measurement devices under respective sets of measuring conditions that are different from each other;

measuring a measurand of the sample, based upon the first optical measurement;

measuring a measurand of the sample, based upon the second optical measurement;

normalizing the measurand measured based upon the first optical measurement and the measurand measured based upon the second optical measurement, with respect to each other; and determining a parameter of the sample based upon at least one of the normalized measurand measured based upon the first optical measurement and the normalized measurand measured based upon the second optical measurement.

31. Apparatus for use with a biological sample, the apparatus comprising:

at least one computer processor configured to:

perform first and second optical measurements on the sample, using one or more optical measurement devices under respective sets of measuring conditions that are different from each other, measure a measurand of the sample, based upon the first optical measurement, measure a measurand of the sample, based upon the second optical measurement, normalize the measurand measured based upon the first optical measurement and the measurand measured based upon the second optical measurement, with respect to each other, and determine a parameter of the sample based upon at least one of the normalized measurand measured based upon the first optical measurement and the normalized measurand measured based upon the second optical measurement.

32. A computer software product, for use with a biological sample, the computer software product comprising a non-transitory computer-readable medium in which program instructions are stored, which instructions, when read by a computer cause the computer to perform the steps of:

performing first and second optical measurements on a sample, using one or more optical measurement devices under respective sets of measuring conditions that are different from each other;

measuring a measurand of the sample, based upon the first optical measurement;

measuring a measurand of the sample, based upon the second optical measurement;

normalizing the measurand measured based upon the first optical measurement and the measurand measured based upon the second optical measurement, with respect to each other; and determining a parameter of the sample based upon at least one of the normalized measurand measured based upon the first optical measurement and the normalized measurand measured based upon the second optical measurement.

It will be appreciated by persons skilled in the art that the present invention is not limited to what has been particularly shown and described hereinabove. Rather, the scope of the present invention includes both combinations and subcombinations of the various features described hereinabove, as well as variations and modifications thereof that are not in the prior art, which would occur to persons skilled in the art upon reading the foregoing description.

The invention claimed is:

1. A method for use with a blood sample, the method comprising:

measuring hematocrit within the blood sample, by performing a first measurement on a first portion of the blood sample;

measuring mean corpuscular volume in the blood sample, by performing a second measurement on a second portion of the blood sample, the second portion being diluted with respect to the first portion;

determining a red blood cell count per unit volume within the blood sample, by dividing the hematocrit measured within the first portion by the mean corpuscular volume measured within the second portion; and determining counts of one or more components per unit volume within the blood sample, based on the red blood cell count per unit volume within the blood sample, by:

analyzing a microscopic image of at least one of the first and second portions of the blood sample, such as to determine a count of the one or more components and count of red blood cells within the at least one of the first and second portions of the blood sample, determining a ratio between the count of the one or more components and the count of red blood cells within the at least one of the first and second portions of the blood sample, and determining the count of the one or more components per unit volume within the blood sample by multiplying the red blood cell count per unit volume by the ratio.

2. The method according to claim 1, wherein measuring hematocrit within the blood sample comprises performing a measurement on the first portion of the blood sample selected from the group consisting of: a micro-hematocrit-method measurement, an impedance measurement, and an ultrasonic measurement.

3. The method according to claim 1, wherein analyzing the microscopic image of at least one of the first and second portions of the blood sample comprises analyzing a microscopic image of the first portion of the blood sample.

4. The method according to claim 1, wherein analyzing the microscopic image of at least one of the first and second portions of the blood sample comprises analyzing a microscopic image of the second portion of the blood sample.

5. The method according to claim 1, wherein performing the second measurement on the second portion of the blood sample comprises performing microscopic bright-field imaging on the second portion of the blood sample.

6. The method according to claim 1, wherein the one or more components within the blood sample are selected from the group consisting of: red blood cells of a given type, white blood cells, white blood cells of a given type, circulating tumor cells, platelets, platelets of a given type, bacteria, pathogens, pathogens of a given type, reticulocytes, and Howell-Jolly bodies.

7. Apparatus for use with a blood sample, the apparatus comprising:

at least one computer processor configured to:

measure hematocrit in the blood sample, by performing a first measurement on a first portion of the blood sample;

measure mean corpuscular volume in the blood sample, by performing a second measurement on a second portion of the blood sample, the second portion being diluted with respect to the first portion;

determine a red blood cell count per unit volume within the blood sample, by dividing the hematocrit measured within the first portion by the mean corpuscular volume measured within the second portion; and determine counts of one or more components per unit volume within the blood sample, based on the red blood cell count per unit volume within the blood sample, by:
- analyzing a microscopic image of at least one of the first and second portions of the blood sample, such as to determine a count of the one or more components and count of red blood cells within the at least one of the first and second portions of the blood sample,
- determining a ratio between the count of the one or more components and the count of red blood cells within the at least one of the first and second portions of the blood sample, and
- determining the count of the one or more components per unit volume within the blood sample by multiplying the red blood cell count per unit volume by the ratio.

8. The apparatus according to claim 7, wherein the at least one computer processor is configured to perform the first measurement on the first portion of the blood sample by performing a measurement on the first portion of the blood sample selected from the group consisting of: a micro-hematocrit-method measurement, an impedance measurement, and an ultrasonic measurement.

9. The apparatus according to claim 7, wherein the at least one computer processor is configured to analyze the microscopic image of at least one of the first and second portions of the blood sample by analyzing a microscopic image of the first portion of the blood sample.

10. The apparatus according to claim 7, wherein the at least one computer processor is configured to analyze the microscopic image of at least one of the first and second portions of the blood sample by analyzing a microscopic image of the second portion of the blood sample.

11. The apparatus according to claim 7, wherein the at least one computer processor is configured to perform the second measurement on the second portion of the blood sample by performing microscopic bright-field imaging on the second portion of the blood sample.

12. The apparatus according to claim 7, wherein the one or more components within the blood sample are selected from the group consisting of: red blood cells of a given type, white blood cells, white blood cells of a given type, circulating tumor cells, platelets, platelets of a given type, bacteria, pathogens, pathogens of a given type, reticulocytes, and Howell-Jolly bodies.

13. A computer software product, for use with a blood sample, the computer software product comprising a non-transitory computer-readable medium in which program instructions are stored, which instructions, when read by a computer cause the computer to perform the steps of:
- measuring hematocrit within the blood sample, by performing a first measurement on a first portion of the blood sample;
- measuring mean corpuscular volume in the blood sample, by performing a second measurement on a second portion of the blood sample, the second portion being diluted with respect to the first portion; and
- determining a red blood cell count per unit volume within the blood sample, by dividing the hematocrit measured within the first portion by the mean corpuscular volume measured within the second portion; and
- determining counts of one or more components per unit volume within the blood sample, based on the red blood cell count per unit volume within the blood sample, by:
  - analyzing a microscopic image of at least one of the first and second portions of the blood sample, such as to determine a count of the one or more components and count of red blood cells within the at least one of the first and second portions of the blood sample,
  - determining a ratio between the count of the one or more components and the count of red blood cells within the at least one of the first and second portions of the blood sample, and
  - determining the count of the one or more components per unit volume within the blood sample by multiplying the red blood cell count per unit volume by the ratio.

\* \* \* \* \*